United States Patent
Feldman et al.

(10) Patent No.: US 11,048,694 B2
(45) Date of Patent: Jun. 29, 2021

(54) MEDIAN BASED ESTIMATION OF DATABASE QUERY RESPONSES

(71) Applicant: INTERNATIONAL BUSINESS MACHINES CORPORATION, Armonk, NY (US)

(72) Inventors: Vitaly Feldman, Mountain View, CA (US); Thomas Steinke, Mountain View, CA (US)

(73) Assignee: International Business Machines Corporation, Armonk, NY (US)

( * ) Notice: Subject to any disclaimer, the term of this patent is extended or adjusted under 35 U.S.C. 154(b) by 518 days.

(21) Appl. No.: 15/963,436

(22) Filed: Apr. 26, 2018

(65) Prior Publication Data
US 2019/0332703 A1 Oct. 31, 2019

(51) Int. Cl.
*G06F 16/2458* (2019.01)
*G06F 16/242* (2019.01)
*G16H 10/60* (2018.01)
*G06N 7/00* (2006.01)
*G06N 20/00* (2019.01)
*G06F 16/2457* (2019.01)
*G06F 16/27* (2019.01)

(52) U.S. Cl.
CPC ...... *G06F 16/2425* (2019.01); *G06F 16/2462* (2019.01); *G06F 16/24578* (2019.01); *G06F 16/278* (2019.01); *G06N 7/005* (2013.01); *G06N 20/00* (2019.01); *G16H 10/60* (2018.01)

(58) Field of Classification Search
CPC .... G06F 16/24; G06F 16/278; G06F 16/2471; G06F 16/248; G06F 16/24532

USPC .................................................. 707/755, 770
See application file for complete search history.

(56) References Cited

U.S. PATENT DOCUMENTS

| | | | |
|---|---|---|---|
| 5,878,426 A | 3/1999 | Plasek et al. | |
| 7,047,230 B2 | 5/2006 | Gibbons | |
| 7,761,462 B2 | 7/2010 | Bjornson et al. | |
| 2010/0005056 A1* | 1/2010 | Bayliss | G06F 16/24578 707/E17.005 |
| 2015/0169688 A1* | 6/2015 | Halverson | G06F 16/24554 707/718 |

(Continued)

OTHER PUBLICATIONS

Grace Period Disclosure under 35 U.S.C. § 102(b)(1)(A): Vitaly et al.; "Generalization for Adaptively-chosen Estimators via Stable Median"; Proceedings of Machine Learning Research vol. 65:1-30, Jun. 20, 2017.

(Continued)

*Primary Examiner* — Marcin R Filipczyk
(74) *Attorney, Agent, or Firm* — Aaron N. Pontikos (57) ABSTRACT

A computer system may include a processor and a memory coupled thereto. The memory may include a database. The processor may be configured to randomly split the database into sub-databases and applying a database query to the sub-databases. The processor may also be configured to generate respective estimated query response values for each sub-database based upon applying the database query, calculate a median of the estimated query response values, and generate a probability distribution based upon the estimated query response values and the calculated median. The processor may further be configured to select a final estimated query response value based upon the probability distribution.

17 Claims, 2 Drawing Sheets

(56) References Cited

U.S. PATENT DOCUMENTS

| | | | |
|---|---|---|---|
| 2017/0024452 A1 | 1/2017 | Budalakoti et al. | |
| 2018/0060750 A1* | 3/2018 | Sheppard | H04N 21/44213 |
| 2018/0314735 A1* | 11/2018 | Liu | G06F 16/217 |

OTHER PUBLICATIONS

Anonymously; "A Systemic Design for Random Sampling," IP.com Disclosure No. IPCOM000241381D, Apr. 21, 2015. Retrieved from Internet using: http://priorart.ip.com/IPCOM/000241381#.

F. Olken, and D. Rotem, "Simple Random Sampling from Relational Databases," Proceedings of the Twelfth International Conference on VLDB, Kyoto, (Aug. 1986), pp. 160 169. Retrieved from Internet using: https://pubarchive.lbl.gov/islandora/object/ir:88270/datastream/PDF/download/citation.pdf.

Bassily et al., "Algorithmic Stability for Adaptive Data Analysis", arXiv:1511.02513v1 [cs.LG] Nov. 8, 2015, 30 pages.

Bassily et al., "Algorithmic Stability for Adaptive Data Analysis", STOC'16, Jun. 19-21, 2016, Cambridge, MA, USA, pp. 1046-1059.

Bassily et al., "Typical Stability", arXiv:1604.03336v2 [cs.LG] Sep. 19, 2016, 24 pages.

Blum et al., "A Learning Theory Approach to Non-Interactive Database Privacy", STOC'08, May 17-20, 2008, Victoria, British Columbia, Canada, 9 pages.

Bun et al., "Concentrated Differential Privacy: Simplifications, Extensions, and Lower Bounds", arXiv:1605.02065v1 [cs.CR] May 6, 2016, 52 pages.

Bun et al., "Differentially Private Release and Learning of Threshold Functions", 2015 IEEE 56th Annual Symposium on Foundations of Computer Science, DOI 10.1109/FOCS.2015.45, pp. 634-649.

Bun et al., "Make Up Your Mind: The Price of Online Queries in Differential Privacy", arXiv:1604.04618v1 [cs.CR] Apr. 15, 2016, 37 pages.

Dwork et al., "Boosting and Differential Privacy", 2010 IEEE 51st Annual Symposium on Foundations of Computer Science, DOI 10.1109/FOCS.2010.12, pp. 51-60.

Dwork et al., "Calibrating Noise to Sensitivity in Private Data Analysis", In TCC, 20 pages, 2006a.

Dwork et al., "Differential Privacy and Robust Statistics", STOC'09, May 31-Jun. 2, 2009, Bethesda, Maryland, USA, 10 pages.

Dwork et al., "Generalization in Adaptive Data Analysis and Holdout Reuse", NIPS 2015, 9 pages.

Dwork et al., "On the Complexity of Differentially Private Data Release—Efficient Algorithms and Hardness Results", STOC'09, May 31-Jun. 2, 2009, Bethesda, Maryland, USA, 10 pages.

Dwork et al., "Our Data, Ourselves: Privacy via Distributed Noise Generation", EUROCRYPT 2006, LNCS 4004, pp. 486-503, 2006.

Dwork et al., "Preserving Statistical Validity in Adaptive Data Analysis", arXiv:1411.2664v3 [cs.LG] Mar. 2, 2016, 29 pages.

Dwork et al., "Preserving Statistical Validity in Adaptive Data Analysis", STOC'15, Jun. 14-17, 2015, Portland, Oregon, USA, pp. 117-126.

Dwork et al., "The Algorithmic Foundations of Differential Privacy", Foundations and TrendsTrends in Theoretical Computer Science vol. 9, Nos. 3-4 (2014), 281 pages.

Dwork et al., "The reusable holdout: Preserving validity in adaptive data analysis", Science, Aug. 7, 2015, vol. 349, Issue 624, pp. 636-638.

Feldman, Vitaly, "Dealing with Range Anxiety in Mean Estimation via Statistical Queries", arXiv:1611.06475v2 [cs.LG] Aug. 26, 2017, 11 pages.

Hardt et al., "A Multiplicative Weights Mechanism for Privacy-Preserving Data Analysis", 2010 IEEE 51st Annual Symposium on Foundations of Computer Science, DOI 10.1109/FOCS.2010.85, pp. 61-70.

Hardt et al., "Preventing False Discovery in Interactive Data Analysis is Hard", arXiv:1408.1655v1 [cs.LG] Aug. 6, 2014, 31 pages.

Kairouz et al. "The Composition Theorem for Differential Privacy", arXiv:1311.0776v4 [cs.DS] Dec. 6, 2015, 32 pages.

Kearns, Michael, "Efficient Noise-Tolerant Learning from Statistical Queries", Journal of the ACM, vol. 45, No. 6, Nov. 1998, pp. 983-1006.

McSherry et al., "Mechanism Design via Differential Privacy", 48th Annual IEEE Symposium on Foundations of Computer Science, DOI 10.1109/FOCS.2007.66, pp. 94-103.

Nissim et al., "Concentration Bounds for High Sensitivity Functions Through Differential Privacy", arXiv:1703.01970v1 [cs.LG] Mar. 6, 2017, 27 pages.

Nissim et al., "CS 227r: Topics in Cryptography and Privacy", Course Outline, Harvard University Privacy Tools Project, retrieved from the Internet on Sep. 29, 2020, 2 pages.

Nissim et al., "Smooth Sensitivity and Sampling in Private Data Analysis", STOC'07, Jun. 11-13, 2007, San Diego, California, USA, 10 pages.

Rogers et al., "Max-Information, Differential Privacy, and Post-Selection Hypothesis Testing", 2016 IEEE 57th Annual Symposium on Foundations of Computer Science, DOI 10.1109/FOCS.2016.59, pp. 487-494.

Roth et al., "Interactive Privacy via the Median Mechanism", STOC'10, Jun. 5-8, 2010, Cambridge, Massachusetts, USA, pp. 765-774.

Russo et al., "Controlling Bias in Adaptive Data Analysis Using Information Theory", Appearing in Proceedings of the 19th International Conference on Artificial Intelligence and Statistics (AISTATS) 2016, Cadiz, Spain, JMLR: W&CP vol. 41, pp. 1232-1240.

Smith, Adam, "Privacy-preserving Statistical Estimation with Optimal Convergence Rates", TOC'11, Jun. 6-8, 2011, San Jose, California, USA, 9 pages.

Steinke et al., "Between Pure and Approximate Differential Privacy", arXiv:1501.06095v1 [cs.DS] Jan. 24, 2015, 15 pages.

Steinke et al., "Interactive Fingerprinting Codes and the Hardness of Preventing False Discovery", JMLR: Workshop and Conference Proceedings vol. 40:1-41, 2015, 41 pages.

Steinke et al., "Subgaussian Tail Bounds via Stability Arguments", arXiv:1701.03493v2 [cs.DM] Apr. 21, 2017, 11 pages.

* cited by examiner

FIG. 1

MEDIAN BASED ESTIMATION OF DATABASE QUERY RESPONSES

STATEMENT REGARDING PRIOR DISCLOSURES BY THE INVENTORS

The following disclosure is submitted under 35 U.S.C. § 102(b)(1)(A): "Generalization for Adaptively-chosen Estimators via Stable Median"; Vitaly Feldman, Thomas Steinke; Proceedings of Machine Learning Research vol 65:1-30, Jun. 20, 2017.

BACKGROUND

The present invention relates to computer systems, and more specifically, to database querying and related methods.

A database that includes data points selected randomly from a larger population may be queried for a pattern. The pattern, however, may not fully generalize the entire population or data points in the database, but instead, may occur by chance.

Modern data analysis may be considered an iterative process in which multiple algorithms are run on the same data points, often in an adaptive fashion. The algorithms used in each step of the iterative process may depend on the results from previous steps. Human decisions may also introduce additional, implicit dependencies between the data and the algorithms being run. In contrast, theoretical analysis in machine learning and statistical inference generally focuses on fixed and pre-specified algorithms run on "fresh" data.

SUMMARY

A computer system may include a processor and a memory coupled thereto. The memory may include a database. The processor may be configured to randomly split the database into a plurality of sub-databases, and apply a database query to the plurality of sub-databases. The processor may also be configured to generate a plurality of respective estimated query response values for each sub-database based upon applying the database query, calculate a median of the estimated query response values, generate a probability distribution based upon the estimated query response values and the calculated median, and select a final estimated query response value based upon the probability distribution.

The processor may be configured to generate the probability distribution by at least weighting the plurality of estimated query response values based upon proximity to the calculated median. The processor may be configured to select the final estimated query response by at least selecting one of the weighted plurality of respective estimated query response values based upon the weighting as the final estimated query response, for example.

The processor may be configured to generate the probability distribution by at least sampling each of the plurality of estimated query response values based upon $e^{-\epsilon|a_v - b_v|}$ wherein $\epsilon$ is a predetermined parameter, $a_v$ is a number of the estimated query response values greater than the selected estimated query response value, and $b_v$ is a number of the estimated query response values less than the selected estimated query response value.

Each of the plurality of estimated query response values may be sampled from a set of possible query response values proportional to $e^{-\epsilon|a_v - b_v|}$, for example.

The processor may be configured to determine $\epsilon$ according to $$\epsilon = \frac{\log_e |T| + 6}{m},$$

wherein T is a set of possible query response values. The processor may be configured to generate the probability distribution so that the probability distribution at any point is given by $$\frac{P}{e^{-\epsilon l}}$$

wherein P is the probability distribution, and l is a number of points between a given estimated query response value and the median, for example. The database may include a medical database of patient medical data. The database may include a machine learning database, for example.

Another aspect is directed to a computer-implemented method for estimating a response to a database query. The method may include randomly splitting the database into a plurality of sub-databases, applying a database query to the plurality of sub-databases, and generating a plurality of respective estimated query response values for each sub-database based upon applying the database query. The method may also include calculating a median of the estimated query response values and generating a probability distribution based upon the estimated query response values and the calculated median. The method may further include selecting a final estimated query response value based upon the probability distribution.

Another aspect is directed to a computer-readable medium for estimating a response to a database query. The computer-readable medium may include computer-executable instructions that when executed by a processor cause the processor to perform operations that may include randomly splitting the database into a plurality of sub-databases, applying a database query to the plurality of sub-databases, and generating a plurality of respective estimated query response values for each sub-database based upon applying the database query. The operations may also include calculating a median of the estimated query response values, generating a probability distribution based upon the estimated query response values and the calculated median, and selecting a final estimated query response value based upon the probability distribution.

DETAILED DESCRIPTION

Figure 1:
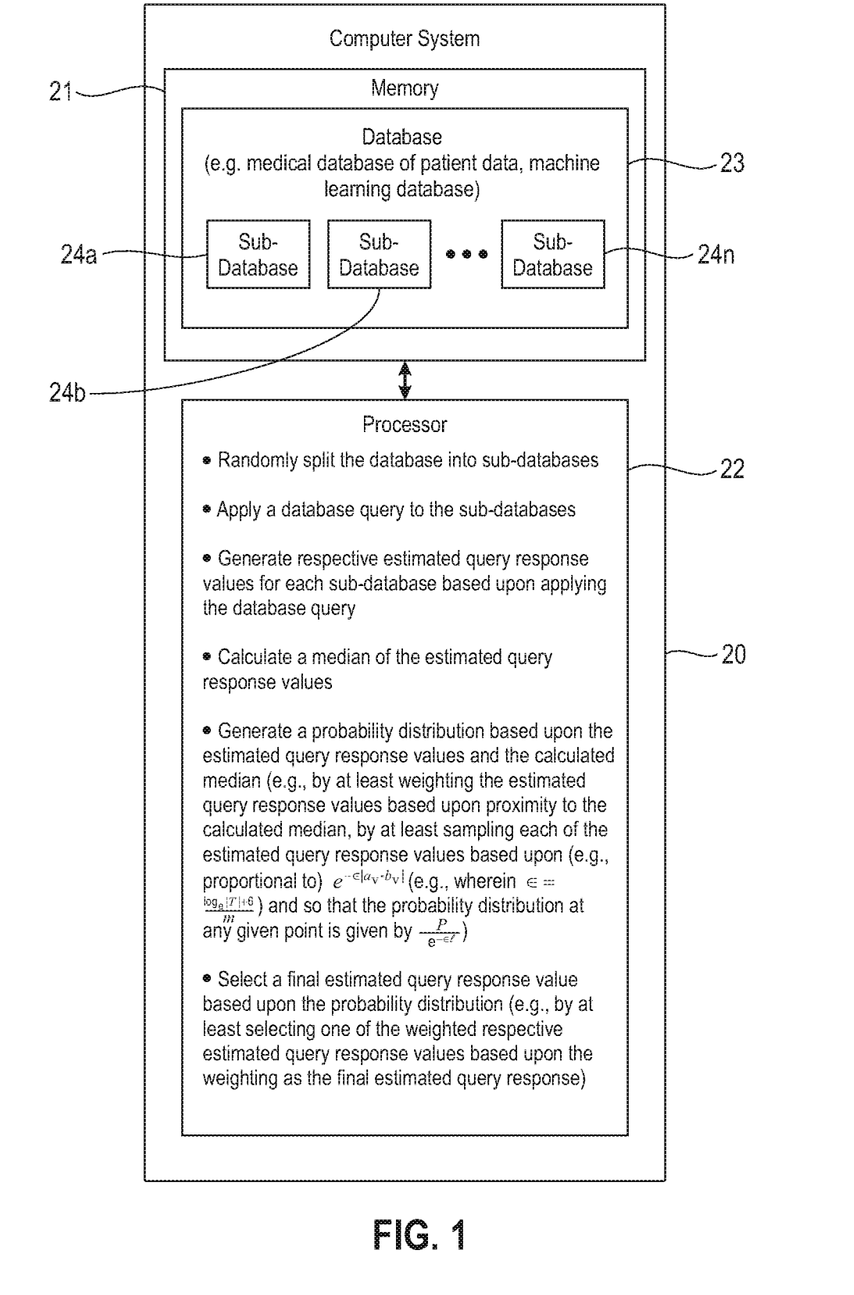
FIG. 1 is a schematic block diagram of a computer system according to an embodiment.
Figure 2:
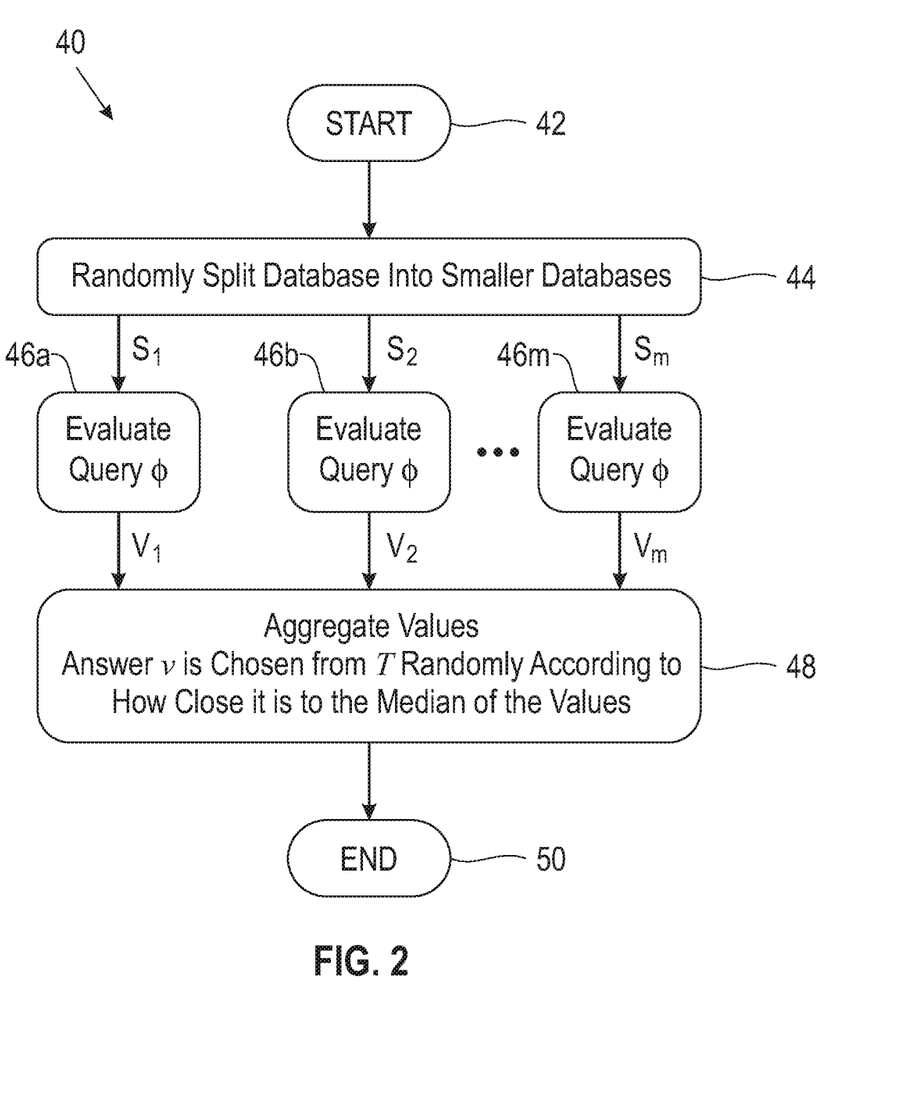
FIG. 2 is a flow diagram of operation of the computer system of FIG. 1.

Referring initially to FIG. 1 and the flowchart 40 in FIG. 2, a computer system 20 for estimating queries includes a memory 21 and a processor 22 coupled to the memory. The memory 21 includes a database 23, which may include, for example, medical data.

Beginning at Block 42, the processor 22 randomly splits the database 23 into smaller sub-databases 24a-24n (Block 44). More particularly, the database 23 ("Database 5"), as an input that includes n samples, is split into sub-databases 24a-24n that includes subsamples $S_1, S_2, \ldots, S_m$ each including t samples. Random disjoint subsets may be chosen so that $$m = \left\lfloor \frac{n}{t} \right\rfloor.$$

The processor 22 applies a database query φ to the sub-databases 24a-24n and generates respective estimated query response values for each sub-database based upon applying the database query (Blocks 46a-46m). The processor 22 calculates a median of the estimated query response values and generates a probability distribution based upon the estimated query response values and the calculated median. The processor 22 may generate the probability distribution by at least weighting the estimated query response values based upon proximity to the calculated median.

The processor 22 selects a final estimated query response value based upon the probability distribution. The processor 22 may select the final estimated query response value based upon the weighting. In other words, the processor 22 aggregated the estimated query response values and the answer v is chosen from T randomly according to how close it is to the median of the value, as will be explained in further detail below (Block 48) before ending at Block 50.

More particularly, the processor 22, for each query φ and response range T performs the following:
- a. Evaluates the query φ on each of the subsamples to obtain values $v_1=\phi(S_1), v_2=\phi(S_2) \ldots, v_m=\phi(S_m)$ (Blocks 46a, 46b, ... 46m);
- b. Selects a value v from T randomly according to a weighting that prioritizes values close to the median of obtained values: $v_1, v_2, \ldots, v_m$. (Block 48). One technique for this selection includes sampling each v from T based upon, for example, proportional to, $e^{-\epsilon|a_v - b_v|}$. Here ε is a predetermined parameter selected prior to selecting the value v. In some embodiments, ε may be set according to, $$\epsilon = \frac{\log_e |T| + 6}{m},$$

wherein $a_v$ is the number of values $v_1, v_2, \ldots, v_m$ that are greater than v (i.e., $v_i > v$), and $b_v$ is the number of values $v_1, v_2, \ldots, v_m$ that are less than v (i.e., $v_i < v$); and
- c. Returns the randomly sampled value v as the answer to the query φ.

The processor 22, according to the algorithm it is executing, also sets the set T of possible response values, which is provided as an input along with the query to the algorithm. The set can be specified explicitly or given as a range of values[A, B] with step size z. Thus, T={A, A+z, A+2z, ..., B-z,B}. If z is not given then the preferred value is set as z=(B−A)/t. As described above, the representative value v is chosen from the set T.

As will be appreciated by those skilled in the art, the system advantageously answers multiple queries in a manner that responses are increasingly accurate even when each query is chosen in a way that depends on the answers returned for previous queries. The computer system 20 may thus answer arbitrary numerical (real-valued) queries.

In contrast to the computer system 20, prior art approaches for answering queries may include running each query on the whole database once and using the value, running each query on a single random subset of the dataset and using the value, and running each query on several random subsets and using the median of the values. However, all of these approaches are known to produce answers that have a relatively low accuracy for the population on common sequences of queries that depend on each other. For example, in a binary classification problem, a standard sequence of queries arises as follows: (i) Use queries to find variables that are noticeably positively correlated with the label (e.g. more than two standard deviations larger than 0); (ii) Build a classifier that takes a majority vote of the selected positively correlated variables; and (iii) Use a further query to estimate the accuracy of this classifier. This classifier will often predict the label on the database much better than on the population. Therefore the final query that measures the accuracy of this classifier cannot be accurately answered by simply evaluating the query on the whole database and using that value. One prior art approach that addresses risks to accuracy that arise from dependencies between the queries is a different algorithm that evaluates the numerical query once and then adds a randomly chosen value to it. This algorithm is only known to provide accurate responses to certain types of queries (namely those whose value has low numerical sensitivity to each data point) and has a fixed level of accuracy. In contrast, the computer system 20 provides increased accuracy responses to arbitrary numerical queries and exploits the variability of the value of the query on the database.

1. Detailed System And Algorithm

Further details of the computer system 20 will now be described. The computer system 20 of the present embodiments demonstrates that a relatively straightforward algorithm may provide increasingly accurate answers to adaptively-chosen queries corresponding to arbitrary real-valued estimators. Specifically, let $\phi: X^t \to \mathbb{R}$ be an arbitrary estimator, where the expectation $E_{z \sim p^t}[\phi(Z)]$ is equal (in which case the estimator is referred to as unbiased) or sufficiently close to some parameter or value of interest. The number of samples t that φ uses corresponds to the desired estimation accuracy (naturally, larger values of t allow more accurate estimators). The present algorithm estimates the expectation $E_{z \sim p^t}[\phi(Z)]$ to within (roughly) the standard deviation of φ(Z)—i.e. $\tau \approx sd(\phi(p^t)) = \sqrt{Var_{z \sim p^t}[\phi(Z)]}$—or, more generally, to within the interquartile range of the distribution of φ on fresh data (i.e. the distribution of φ(Z) for $Z \sim \mathcal{P}^t$, which is denoted by $\phi(\mathcal{P}^t)$). If $$\phi(s) = \frac{1}{t} \sum_{i=1}^{t} \psi(s_i)$$

for a function $\psi: X \to [-1,1]$, then the error roughly scales as $\tau \approx sd(\psi(\mathcal{P}))/\sqrt{t}$. This gives a natural interpretation of t as an accuracy parameter.

In contrast, given a comparable number of samples, existing algorithms for statistical queries give an estimate with accuracy roughly $\tau \approx \sqrt{1/t}$ regardless of the variance of the query. This is not just an artifact of existing analysis since, to ensure the desired level of differential privacy, this algorithm adds noise whose standard deviation scales as $\sqrt{1/t}$. For a statistical query, $\psi: X \to [-1,1]$, the standard deviation of $\psi(\mathcal{P})$ is upper bounded by 1, but is often much smaller. For example, when estimating the accuracy of a binary classifier with (low) error p the present algorithm will give an estimate with accuracy that scales as $\sqrt{p/t}$, rather than $\sqrt{1/t}$.

The algorithm implemented by the system 20 will now be described more formally starting with a relatively simple case of statistical queries. Given a statistical query $\psi: X \to [-1,1]$ and t fresh random i.i.d. samples $Z \in X^t$ drawn from $\mathcal{P}$, the empirical mean estimator $$\phi(Z) \doteq \frac{1}{t} \sum_{i \in [t]} \psi(Z_i)$$

is an unbiased estimator of $E_{X \sim p}[\psi(X)]$, with a standard deviation equal to $sd(\psi(P))/\sqrt{t}$. Applied to such estimators, the algorithm answers adaptively-chosen statistical queries with accuracy that scales as $sd(\psi(\mathcal{P}))/\sqrt{t}$.

Theorem 1.1: For all $\zeta > 0$, $t \in \mathbb{N}$, $\beta > 0$, $k \in \mathbb{N}$, and $n \geq n_0 = O(t \sqrt{k \log(1/\beta)} \log(k/\beta\zeta))$, there exists an efficient algorithm M that, given n samples from an unknown distribution p, provides answers $v_1, \ldots, v_k \in [-1,1]$ to an adaptively-chosen sequence of queries $\psi_1, \ldots, \psi_k: X \to [-1,1]$ and satisfies:

$$\Pr_{\substack{S \sim \mathcal{P}^n \\ M(S)}} \left[ \forall j \in [k] \left| v_j - E_{X \sim \mathcal{P}}[\psi_j(X)] \right| \leq 2 \cdot \frac{sd(\psi_j(\mathcal{P}))}{\sqrt{t}} + \zeta \right] \geq 1 - \beta.$$

Note that the present algorithm also has an additional $\zeta$ precision term. The dependence of sample complexity on $1/\zeta$ is logarithmic and can be further improved using more involved algorithms. Thus the precision term, $\zeta$, like the failure probability $\beta$, can be made negligibly small at little cost. Prior technique give an error bound of $\sqrt{1/t}$, which is at least as large (up to constant factors) as the bound $sd(\psi_j(\mathcal{P}))/\sqrt{t} + \zeta$, when $\zeta \leq 1/t$. For comparison, in the non-adaptive setting the same error may be obtained using $n = O(t \log(k/\beta))$ samples (with $\zeta = 1/t$).

Note that, for simplicity, in Theorem 1.1 the range of each query is normalized to $[-1,1]$. However this normalization affects only the precision term $\zeta$. In particular, for queries whose range is in an interval of length at most b, the number of samples desired for the result to get precision $\zeta$ scales logarithmically in $b/\zeta$. In contrast, the sample complexity of previous results scales quadratically in b. Further, a more refined statement discussed below allows handling queries with arbitrary range.

For general real-valued estimators of the form $\phi: X^t \to [-1,1]$, the algorithm gives the following: (For simplicity it is assumed that t is fixed for all the queries.)

Theorem 1.2 For all $\zeta > 0$, $t \in \mathbb{N}$, $\beta > 0$, $k \in \mathbb{N}$, and $n \geq n_0 = O(t \sqrt{k \log(1/\beta)} \log(k/\beta\zeta))$, there exists an efficient algorithm M that, given n samples from an unknown distribution $\mathcal{P}$, provides answers $v_1, \ldots, v_k \in [-1,1]$ to an adaptively-chosen sequence of queries $\phi_1, \ldots, \phi_k: X^t \to [-1,1]$ and satisfies:

$$\Pr_{\substack{S \sim \mathcal{P}^n \\ M(S)}} \left[ \forall j \in [k] \left| v_j - E_{Z \sim \mathcal{P}^t}[\phi_j(Z)] \right| \leq 2 \cdot sd(\phi_j(\mathcal{P}^t)) + \zeta \right] \geq 1 - \beta.$$

For general estimators, prior technique given accuracy or accuracy guarantees in terms of the worst-case sensitivity. More formally, for $\phi: X^n \to \mathbb{R}$, let $\Delta(\phi)$ denote the worst-case sensitivity of $\phi$—that is, $\Delta(\phi) = \max_{z,z'} \phi(z) - \phi(z')$, where the maximum is over z, $z' \in X^n$ that differ in a single element. Prior techniques and analysis show that for k adaptively-chosen queries $\phi_1, \ldots, \phi_k$, each query $\phi_i$, can be answered with accuracy $$\sqrt{n \cdot \sqrt{k}} \cdot \Delta(\phi_i)$$

(ignoring logarithmic factors and the dependence on the confidence $\beta$). This setting is somewhat more general than the seeing in the present algorithm, since each query is applied to the entire dataset available to the algorithm, whereas with respect to the present setting, each query is applied to fixed-size sub-samples of the dataset. This means that in this setting, the space of estimators that can be applied to data is richer than the present space of estimators and might allow better estimation of some underlying quantity of interest. At the same time, the present techniques give better accuracy guarantees for finding the expectation of each estimator.

To see the difference between the present setting and that in prior approaches, consider estimation of the lowest expected loss of a function from a family $\mathcal{F}$, namely $L^* \doteq \min_{f \in \mathcal{F}} E_{X \sim \mathcal{P}}[L(f, X)]$, where $L: \mathcal{F} \times X \to [-R, R]$ is some loss function. Given a dataset s of size n, the standard ERM estimator is defined as $$\phi_n(s) \doteq \min_{f \in \mathcal{F}} \frac{1}{n} \sum_{i \in [n]} L(f, s_i).$$

Using uniform convergence results, one can often obtain that $|L^* - E_{S \sim \mathcal{P}^n}[\phi_n(S)]| = O(d/\sqrt{n})$, for some d that measures the capacity of $\mathcal{F}$ and also depends on L. The sensitivity of the estimator $\phi_n$ is upper bounded by $2R/n$. Thus prior art algorithms give an estimate of $E_{S \sim \mathcal{P}^n}[\phi_n(S)]$ within (roughly)

$$R \cdot \sqrt{\frac{\sqrt{k}}{n}}$$

and an upper bound on the total error will scale as $(d + R \cdot k^{1/4})/\sqrt{n}$. In the present setting, the estimator $\phi_t$ will be used, where t scales as $n/\sqrt{k}$. The bias of this estimator is $|L^* - E_{S \sim \mathcal{P}^t}[\phi_t(S)]| = O(d/\sqrt{t}) = O(d \cdot k^{1/4}/\sqrt{n})$. At the same time $E_{S \sim \mathcal{P}^t}[\phi_t(S)]$ can be estimated within (roughly) the standard deviation of $\phi_t$. The standard deviation of $\phi_t$ is typically always upper bounded by $2R \cdot \sqrt{t} = R \cdot k^{1/4}/\sqrt{n}$, but is often much smaller. Hence, depending on the setting of the parameters and the distribution $\mathcal{P}$, the present approach described herein gives an error bound that is either higher by a factor of $k^{1/4}$ or lower by a factor of R/d than the prior art approaches. In other words, the prior art approaches and the present approach provide incomparable guarantees for this problem.

Both Theorem 1.2 and Theorem 1.1 are corollaries of the following more general result. Define $$qi_{\mathcal{D}}(a,b) := \{v \in \mathbb{R} : \Pr_{Y \sim \mathcal{D}}[Y \leq v] > a \wedge \Pr_{Y \sim \mathcal{D}}[Y < v] < b\}$$

to be the (a, b)-quantile interval of the distribution $\mathcal{D}$. The (¼,¾)-quantile interval is referred to as the interquartile interval.

Theorem 1.3:

For all $T \subset \mathbb{R}$ with $|T|<\infty$, $t \in \mathbb{N}$, $\beta>0$, $k \in \mathbb{N}$, and $n \geq n_0 = O(t\sqrt{k\log(1/\beta)}\log(|T|k/\beta))$, there exists an efficient algorithm M that, given n samples from an unknown distribution $\mathcal{P}$, provides answers $v_1, \ldots, v_k \in T$ to an adaptively-chosen sequence of queries $\phi_1, \ldots, \phi_k : X^t \to T$ and satisfies:

$$\Pr_{\substack{S \sim \mathcal{P}^n \\ M(S)}}\left[\forall j \in [k] v_j \in qi_{\phi_j(\mathcal{P}^t)}\left(\frac{1}{4}, \frac{3}{4}\right)\right] \geq 1 - \beta.$$

Two remarks may be made about the guarantee of the theorem:

Accuracy in Terms of Interquartile Interval:

The accuracy guarantee of Theorem 1.3 is that each returned answer lies in the (¼,¾)-quantile interval of the distribution of the query function on fresh data (i.e. the distribution $\phi(\mathcal{P}^t)$). The length of this interval is referred to as the interquartile range. This guarantee may appear strange at first sight, but it is actually a strengthening of Theorem 1.2 by Chebyshev's inequality, the interquartile interval of any distribution $\mathcal{D}$ lies within two standard deviations of the mean:

$$qi_{\mathcal{D}}\left(\frac{1}{4}, \frac{3}{4}\right) \subseteq [\underset{Y \sim \mathcal{D}}{E}[Y] - 2 \cdot sd(\mathcal{D}), \underset{Y \sim \mathcal{D}}{E}[Y] - 2 \cdot sd(\mathcal{D})].$$

However, the interquartile interval may be significantly smaller if $\mathcal{D}$ is heavy-tailed. If, for example, the distribution $\mathcal{D}$ has infinite variance, then the present guarantee is still useful, whereas bounds in terms of standard deviation will be meaningless. This formulation does not even assume that the quantity of interest is the expectation of $\phi(\mathcal{P}^t)$ (or even that this expectation exists). In fact, $\phi$ could be a biased estimator of some other parameter of interest.

Intuitively, this accuracy guarantee may be interpreted as follows. If it is know that a sample from $\phi(\mathcal{P}^t)$ is an acceptable answer with probability at least ¾, and the set of acceptable answers forms an interval, then with high probability the answer returned by the present algorithm is acceptable. The constants ¼ and ¾ are, of course, arbitrary. More generally, $v_j \in qi_{\phi_j(\mathcal{P}^t)}(a, b)$ for any $0 \leq a < b \leq 1$ may be demanded. However, this reduction increases the sample complexity $n_0$ by a factor of $1/(b-a)^2$.

Finite Range T:

Theorem 1.3 assumes that the queries have a finite range. This is necessary for the present algorithm, as the required number of samples grows with the size of T, albeit slowly. Using a more involved algorithm, it may be possible to improve the dependence on the size of T from $O(\log|T|)$ to $2^{O(\log^*|T|)}$, where log* denotes the iterated logarithm—an extremely slow-growing function. To obtain Theorem 1.2 from Theorem 1.3, T is set to be the discretization of [−1,1] with granularity and round the output of $\phi: X^t \to [−1,1]$ to the nearest point in T; this introduces the additive error $\zeta$.

However, allowing T to be arbitrary provides further flexibility. For example, T could be a grid on a logarithmic scale, yielding a multiplicative, rather than additive, accuracy guarantee. Furthermore, in some settings the range of the query is naturally finite and the scale-free guarantee of Theorem 1.3 comes at no additional cost. It should also be noted that, in general, the present result allows a different $T_j$ to be chosen (adaptively) for each query $\phi_j$ as long as the size of each $T_j$ is upper-bounded by some fixed value.

Another advantage of this formulation is that it removes the dependence on the entire range of $\phi$: If it is known that the interquartile interval of $\phi(\mathcal{P}^t)$ lies in some interval [a, b], the output range of $\phi$ to [a, b] may be truncated (and then discretize if desired). This operation does not affect the interquartile interval of $\phi(\mathcal{P}^t)$, and hence does not affect the guarantees of the present algorithm. In particular, this means that in Theorem 1.2 the range of each $\phi$ is bounded in [−1,1] does not need to be assumed; it is sufficient to assume that the interquartile interval of $\phi(\mathcal{P}^t)$ lies in [−1,1] to obtain the same guarantee. For example, if it is known beforehand that the mean of $\phi(\mathcal{P}^t)$ lies in [−1,1], and its standard deviation is at most 1, then the range of $\phi$ may be truncated to [−3,3].

Verification Queries:

Queries that ask for "verification" of a given estimate of the expectation of a given estimator will not be considered—each query is specified by a function $\phi: X^t \to \mathbb{R}$ and a value (or "guess") $v \in \mathbb{R}$. The task of the present algorithm is to check whether or not $v \in qi_{\phi(\mathcal{P}^t)}(\rho, 1-\rho)$ for some $\rho$ chosen in advance. Such queries are used in a reusable holdout setting and in the EffectiveRounds algorithm that uses fresh subset of samples when a verification query fails. Provided is an algorithm for answering adaptively-chosen verification queries with the following guarantees.

Theorem 1.4 For all $\alpha$, $\beta$, $\rho \in (0, 1/4)$ with $\alpha < \rho$ and t, l, k, $n \in \mathbb{N}$ with $$n \geq n_0 = O\left(\frac{t\sqrt{l\log\left(\frac{1}{\alpha\beta}\right)}\log\left(\frac{k}{\beta}\right)\rho}{\alpha^2}\right),$$

there exists an efficient algorithm M that, given n samples from an unknown distribution $\mathcal{P}$, provides answers to an adaptively-chosen sequence of queries $(\phi_1, v_1), \ldots, (\phi_k, v_k)$ (where $\phi_j: X^t \to \mathbb{R}$ and $v_j \in \mathbb{R}$ for all $j \in [k]$) and satisfies the following with probability at least $1-\beta$: for all $j \in [k]$ If $v_j \in qi_{\phi_j(\mathcal{P}^t)}(\rho, 1-\rho)$, then the algorithm outputs "Yes".

If $v_j \notin qi_{\phi_j(\mathcal{P}^t)}(\rho-\alpha, 1-\rho+\alpha)$ the algorithm outputs "No".

If neither of these two cases applies, the algorithm may output either "Yes" or "No."

However, once the algorithm outputs "No" in response to l queries, it stops providing answers.

To answer the l queries that do not pass the verification step the present algorithm may be used for answering queries in Theorem 1.3 (with k there set to 1 here).

Answering Many Queries:

Finally, described herein is an (inefficient) algorithm that requires a dataset whose size scales as log k at the expense of an additional $\sqrt{t\log|X|}$ factor.

Theorem 1.5

For all $T \subset \mathbb{R}$ with $|T|<\infty$, $t \in \mathbb{N}$, $\beta>0$, $k \in \mathbb{N}$, and $$n \geq n_0 = O\left(t^{\frac{3}{2}} \cdot \sqrt{\log|X|\log\left(\frac{1}{\beta}\right)} \cdot \log\left(\frac{k\log|T|}{\beta}\right)\right),$$

there exists an algorithm M that, given n samples from an unknown distribution $\mathcal{P}$ supported on X, provides answers $v_1, \ldots, v_k \in T$ to an adaptively-chosen sequence of queries $\phi_1, \ldots \phi_k: X^t \to T$ and satisfies $$\Pr_{\substack{S \sim \mathcal{P}^n \\ M(S)}}\left[\forall j \in [k] v_j \in qi_{\phi_j(\mathcal{P}^i)}\left(\frac{1}{4}, \frac{3}{4}\right)\right] \geq 1 - \beta.$$

It should be noted that when applied to low-sensitivity queries with $t=1/\tau^2$, this algorithm improves dependence on $|X|$ and $\tau$ from $n=\tilde{O}(\log(|X|)/\tau^4)$ in prior art techniques to $n=\tilde{O}(\sqrt{\log|X|}/\tau^3)$ (although, as pointed out above, the setting in the prior art technique is not always comparable to the present setting).

Techniques

Similar to prior techniques, the present embodiments rely on properties of differential privacy. Differential privacy is a stability property of an algorithm, namely it requires that replacing any element in the input dataset results in a small change in the output distribution of the algorithm. As a result, a function output by a differentially private algorithm on a given dataset generalizes to the underlying distribution. Specifically, if a differentially private algorithm is run on a dataset drawn i.i.d from any distribution and the algorithm outputs a low-sensitivity function, then the empirical value of that function on the input dataset is close to the expectation of that function on a fresh dataset drawn from the same distribution.

The second relatively important property of differential privacy is that it composes adaptively: running several differentially private algorithms on the same dataset still satisfies differential privacy (with somewhat worse parameters) even if each algorithm depends on the output of all the previous algorithms. This property makes it possible to answer adaptively-chosen queries with differential privacy and a number of algorithms have been developed for answering different types of queries. The generalization property of differential privacy then implies that such algorithms can be used to provide answers to adaptively-chosen queries while ensuring generalization.

For each query, the algorithm of Theorem 1.3 first splits its input, including n samples, into m=n/t disjoint subsamples of size t, and computes the estimator $\phi: X^t \to \mathbb{R}$ on each. It then outputs an approximate median of the resulting values in a differentially private manner. Here an approximate median is any value that falling between the $(1-\alpha)/2$-quantile and the $(1+\alpha)/2$-quantile of the m computed values (for some approximation parameter $\alpha$). In addition to making the resulting estimator more stable, this step also amplifies the probability of success of the estimator. For comparison, prior art algorithms compute the estimator once on the whole sample and then output the value in a differentially private manner.

It is thus shown that differential privacy ensures that an approximate empirical median with high probability falls within the true interquartile interval of the estimator on the input distribution. Here, the known strong connection between differential privacy and generalization is relied upon. However, the present embodiments rely on stability to replace of any one of the m subsamples (including t points) used to evaluate the estimator, whereas previous analyses used the stability under replacement of any one out of the n data points. The use of this stronger condition is crucial for bypassing the limitations of previous techniques while achieving improved accuracy guarantees.

A number of differentially-private algorithms for approximating the empirical median of values in a dataset have been studied in the literature. One common approach to this problem is the use of local sensitivity. This approach focuses on additive approximation guarantees and requires stronger assumptions on the data distribution to obtain explicit bounds on the approximation error.

In the present embodiments, a data-dependent notion of approximation to the median is relied upon in which the goal is to output any value v between the $(1-\alpha)/2$-quantile and the $(1+\alpha)/2$-quantile of the empirical distribution for some approximation parameter $\alpha$. It may thus be easy to see that this version is essentially equivalent to the interior point problem in which the goal is to output a value between the smallest and largest values in the dataset. A prior art technique recently showed that the optimal sample complexity of privately finding an interior point in a range of values T lies between $m=2^{(1+o(1))\log^*|T|}$ and $m=\Omega(\log^*|T|)$, where log* is iterated logarithm or inverse tower function satisfying $\log^*(2^x)=1+\log^*(x)$.

The prior art algorithm is relatively complex and, therefore, a simple and efficient algorithm is used herein that is based on an exponential mechanism, and is similar to an algorithm to estimate quantiles of a distribution. This algorithm has sample complexity $m=O(\log|T|)$ (for constant $\alpha > 0$). In addition, for the present algorithm that answers many queries another simple algorithm is used based on approximate binary search, which can yield sample complexity $m=O(\sqrt{\log|T|})$; it has the advantage that it reduces the problem to a sequence of statistical queries. It is generally known that the exponential mechanism and binary search can be used to privately find an approximate median in the context of the applications described herein.

Now the second part of the proof: an approximate empirical median is also in the interquartile interval of the distribution. i.e., any value in the empirical $(\frac{3}{8}, \frac{5}{8})$-quantile interval falls in the distribution's $(\frac{1}{4}, \frac{3}{4})$-quantile interval. A value $v \in T$ is an approximate empirical median if the empirical cumulative distribution function at v is close to $\frac{1}{2}$ that is, $\text{cdf}_S(v) = \Pr_{Y \sim S}[Y \leq v] \approx \frac{1}{2}$, where $S \sim \mathcal{D}^n$ is the random samples and Y~S denotes picking a sample from S randomly and uniformly. Note that $\text{cdf}_S(v)$ is the empirical mean of a statistical query over S, whereas the true cumulative distribution function $\text{cdf}_\mathcal{D}(v) = \Pr_{Y \sim \mathcal{D}}[Y \leq v]$ is the true mean of the same statistical query. Hence, the known strong connection between differential privacy and generalization for statistical queries can be applied to obtain that $\text{cdf}_\mathcal{D}(v) \approx \text{cdf}_S(v)$. This ensures $\text{cdf}_\mathcal{D}(v) \approx \frac{1}{2}$ and hence v falls in $qi_\mathcal{D}(\frac{1}{4}, \frac{3}{4})$ (with high probability).

For estimators that produce an accurate response with high probability (such as any well-concentrated estimator) a different, substantially simpler way to prove high probability bounds on the accuracy of the whole adaptive procedure is provided. This allows bypassing the known proofs of high-probability bounds that rely on relatively involved arguments.

The present algorithm for answering verification queries (Theorem 1.4), is obtained by reducing the verification step to verification of two statistical queries for which the domain of the function is $X^t$ and the expectation is estimated relative to $\mathcal{P}^t$. To further improve the sample complexity, it is observed that it is possible to calibrate the algorithm for verifying statistical queries from to introduce less noise when $\rho$ is small. This improvement relies on sharper analysis of the known generalization properties of differential privacy that has already found some additional uses.

The present algorithm for answering many queries (Theorem 1.5) is also obtained by a reduction to statistical queries over $X^t$. In this case statistical queries are used to find a value in the interquartile interval of the estimator via a binary search.

Finally, the differentially private algorithms that are used to answer queries might also be of interest for applications in private data analysis. These algorithms demonstrate that meaningful privacy and error guarantees can be achieved without any assumptions on the sensitivity of estimators. From this point of view, the present approach is an instance of subsample-and-aggregate technique of a prior art technique, where the approximate median algorithm is used for aggregation. It is noted that a prior technique used a somewhat related approach that also takes advantage of the concentration of the estimator around its mean during the aggregation step. That algorithm first clips the tails of the estimator's distribution via a differentially private quantile estimation and then uses simple averaging with Laplace noise addition as the aggregation step. That analysis is specialized to estimators that are approximately normally distributed and hence the results are not directly comparable with the present more general setting.

2. Preliminaries

For $k \in \mathbb{N}$, it is denoted that $[k] = \{1, 2, \ldots, k\}$ and $a_{[k]}$ is used as a shorthand for the k-tuple $(a_1, a_2, \ldots, a_k)$. For a condition $E$, $\mathbb{1}(E)$ is used to denote the indicator function of E. Thus $E[\mathbb{1}(E)] = \Pr[E]$.

For a randomized algorithm M $Y \sim M$ to denote that Y is random variable obtained by running M. For a distribution $\mathcal{D}$, $Y \sim D$ is used to denote that Y is a random variable distributed according to $\mathcal{D}$. For $0 \le \alpha \le \beta \le 1$ and a distribution $\mathcal{D}$, it denoted by the $(\alpha, \beta)$-quantile interval of $\mathcal{D}$ by $$qi_\mathcal{D}(\alpha,\beta) = \{v \in \mathbb{R} : \Pr_{Y \sim \mathcal{D}}[Y \le v] > \alpha \wedge \Pr_{Y \sim \mathcal{D}}[Y < v] < \beta\}.$$

$qi_\mathcal{D}(\frac{1}{4}, \frac{3}{4})$ is referred to as the interquartile interval of $\mathcal{D}$ and the length of this interval is the interquartile range. For $s \in \mathbb{R}^n$ $qi_s(\alpha, \beta)$ is denoted by the empirical version of the quantity above, that is the $(\alpha, \beta)$-quantile interval obtained by taking $\mathcal{D}$ to be the uniform distribution over the elements of s. In general, the datasets are viewed as being equivalent to a distribution, namely the uniform distribution on elements of that dataset.

For the present algorithms, a query is specified by a function $\phi: X^t \to \mathbb{R}$. For notational simplicity, $\mathcal{Z} = X^t$ and partition a dataset $s \in X^n$ into m points $s_1, \ldots, s_m \in \mathcal{Z}$. Therefore throughout the discussion n=mt. For $s \in \mathcal{Z}^m$, $\phi(s) = (\phi(s_1), \ldots, \phi(s_m))$ is the transformed dataset. Similarly, for a distribution $\mathcal{P}$ on X, $\mathbb{1} = \mathcal{P}^t$ is defined to be the corresponding distribution on $\mathcal{Z}$ and $\phi(\mathbb{1})$ to be the distribution obtained by applying $\phi$ to a random sample from $\mathcal{Z}$. The expectations of these distributions are denoted $$s[\phi] = \frac{1}{m} \sum_{i \in [m]} \phi(s_i) \text{ and } \mathcal{D}[\phi] = E_{Z \sim \mathcal{D}}[\phi(Z)].$$

2.1 Adaptivity

A central topic described herein is the interaction between two algorithms A—the analyst—and M—the present query-answering algorithm. Let Q be the space of all possible queries and $\mathcal{A}$ be the set of all possible answers. In the present applications, Q will be a set of functions $\phi: \mathcal{Z} \to \mathbb{R}$, possibly with some additional parameters and $\mathcal{A}$ will be (a subset of) $\mathbb{R}$. The notation for this interaction is thus:

Input $s \in \mathcal{Z}^m$ is given to M.
For j=1, 2, ..., k:
A computes a query $q_j \in Q$ and passes it to M
M produces answer $a_j \in \mathcal{A}$ and passes it to A
The output is the transcript $(q_1 q_2, \ldots, q_k, a_1, a_2, \ldots, a_k) \in Q^k \times \mathcal{A}^k$ Given interactive algorithms A and M, define $A \leftrightarrows M(s)$ to be function which produces a random transcript of the interaction between A and M, where s is the input given to M. Formally, the above specifies how $A \leftrightarrows M: X^n \to Q^k \times \mathcal{A}^k$ is defined.

The transcript function $A \leftrightarrows M$ provides a "non-interactive view" of the output of an interactive process. The goal is thus to construct M such that, for all A, the output of $A \leftrightarrows M$ has the desired accuracy and stability properties.

2.2 Differential Privacy

Definition 2.1 (Differential Privacy) An algorithm $M: \mathcal{Z}^m \to \mathcal{Y}$ is $(\epsilon, \delta)$-differentially private if, for all datasets s, s' $\in \mathcal{Z}^m$ that differ on a single element, $$\forall E \subseteq \mathcal{Y} \Pr[M(s) \in E] \le e^\epsilon \Pr[M(s') \in E] + \delta.$$

It should be noted that, throughout, an algorithm $M: X^n \to \mathcal{Y}$ is considered whereby $\mathcal{Z} = X^t$ with n=mt so that $M: \mathcal{Z}^m \to \mathcal{Y}$. Then the differential privacy is defined with respect to the latter view (that is, with respect to changing a whole tuple of t elements in the original view of M). This is a stronger condition.

However, Definition 2.1 only covers non-interactive algorithms. Thus, it can extended to interactive algorithms:

Definition 2.2 (Interactive Differential Privacy) An interactive algorithm M is $(\epsilon, \delta)$-differentially private if, for all interactive algorithms A, the (non-interactive) algorithm $A \leftrightarrows M: \mathcal{Z}^m \to \mathcal{Y}$ is $(\epsilon, \delta)$-differentially private.

Theorem 2.3 (Post-processing) Let $M: \mathcal{Z}^m \to \mathcal{Y}$ be $(\epsilon, \delta)$-differentially private. Let $F: \mathcal{Y} \to \mathcal{Y}'$ be an arbitrary randomized algorithm. Define $M': \mathcal{Z}^m \to \mathcal{Y}'$ by $M'(s)=F(M(s))$. Then M' is also $(\epsilon, \delta)$-differentially private.

Post-processing may be considered relatively important as it allows performance of further computation on the output of a differentially private algorithm without breaking the privacy guarantee.

The key adaptive composition property of differential privacy is now stated, which bounds how rapidly differential privacy degrades under repeated use of the same dataset Theorem 2.4 (Prior Adaptive Composition Technique): Fix $k \in \mathbb{N}$ and $\epsilon_1, \ldots, \epsilon_k, \delta_1, \ldots, \delta_k > 0$. Let $M_1, \ldots, M_k: \mathcal{Z}^m \times \mathcal{Y} \to \mathcal{Y}$ be randomized algorithms. Suppose that for all $j \in [k]$ and all fixed $y \in \mathcal{Y}$, the randomized algorithm $x \mapsto M_j(x, y)$ is $(\epsilon_j, \delta_j)$-differentially private. Define $\hat{M}_1, \ldots, \hat{M}_k: \mathcal{Z}^m \to \mathcal{Y}$ inductively by $\hat{M}_1(x) = M_1(x, y_0)$ where $y_0 \in \mathcal{Y}$ is fixed and $\hat{M}_{j+1}(x) = M_{j+1}(x, \hat{M}_j(x))$ for $j \in [k-1]$. Then $\hat{M}_k$ is $(\hat{\epsilon}, \hat{\delta})$-differentially private for $$\hat{\epsilon} = \frac{1}{2} \sum_{j \in [k]} \epsilon_j^2 + \sqrt{2 \log\left(\frac{1}{\delta'}\right) \sum_{j \in [k]} \epsilon_j^2} \text{ and } \hat{\delta} = \delta' + \sum_{j \in [k]} \delta_j,$$

where $\delta' \in (0,1)$ is arbitrary.

The analyst that asks queries can be seen as a post-processing step on the output of a differentially private algorithm that answers the queries. Thus, by combining the adaptive composition and post-processing properties of differential privacy are obtained to ensure that an interactive algorithm is differentially private it is sufficient to ensure that each of the individual queries is answered with differential privacy.

Theorem 2.5: Fix $k \in \mathbb{N}$ and $\varepsilon, \delta > 0$. Let $M: \mathcal{Z}^m \times Q \to \mathcal{A}$ be an algorithm, such that $M(s, q)$ provides an answer to the query q using the dataset s and M is $(\varepsilon, \delta)$-differentially private for every fixed $s \in \mathcal{Z}^m$. Define an interactive algorithm $M^{\oplus k}$ that takes as input $s \in \mathcal{Z}^m$ and answers k adaptively-chosen queries $q_1, \ldots, q_k \in Q$ where, for each $j \in [k]$, $M^{\oplus k}$ produces an answer by independently running $M(s, q_j)$. Then $M^{\oplus k}$ is $(\tfrac{1}{2}k\varepsilon^2 + \varepsilon\sqrt{2k\ln(1/\delta')}, \delta' + k\delta)$-differentially private for all $\delta' \in (0,1)$.

3. Approximate Median

In this section, differentially private algorithms for outputting an approximate median of a real-valued dataset are presented. Namely, for $s \in \mathbb{R}^m$, an $\alpha$-approximate median of s is defined to be any element of the set $$qi_s\left(\frac{1-\alpha}{2}, \frac{1+\alpha}{2}\right).$$

In the present application, each real value is obtained by applying the given query function to a single subsample.

Several differentially private algorithms for computing an approximate median are known. All of these algorithms assume that the input elements and the range of the algorithm are restricted to some finite set $T \subseteq \mathbb{R}$. They describe an $(\varepsilon, \delta)$-differentially private algorithm which, on input $s \in T^m$, outputs an $\alpha$-approximate median of s as long as $m \geq (2+o(1))^{\log^*|T|} \cdot O(\log(1/\varepsilon\delta)/\varepsilon\alpha)$. Consider the problem of outputting an interior point which is equivalent to the definition of a 1-approximate median. However, by removing the elements of the dataset that are not in $$qi_s\left(\frac{1-\alpha}{2}, \frac{1+\alpha}{2}\right)$$

$\alpha$-approximate median reduces to the interior point problem.

Prior techniques also prove a nearly tight lower bound of $m \geq \Omega(\log^*|T|)$ for $\alpha = \varepsilon = 1$ and $\delta = 1/100 \, m^2$. This lower bound implies that privately outputting an approximate median is only possible if the data points are restricted to a finite range. It is noted that that for the stricter $\varepsilon$-differential privacy the sample complexity of this problem for constant $\alpha > 0$ is $\theta(\log(|T|)/\varepsilon)$. Any differentially private algorithm for finding an approximate median can be used in the results. The prior art algorithm in is relatively involved and hence a relatively simple algorithm for the problem that relies on a "folklore" application of the exponential mechanism will be described.

Theorem 3.1: For all $\varepsilon, \alpha, \beta > 0$, finite $T \subset \mathbb{R}$: and all $m \geq 4 \ln(|T|/\beta)/\varepsilon\alpha$, there exists an $(\varepsilon, 0)$-differentially private randomized algorithm M that given a dataset $s \in \mathcal{Z}^m$ and a query $\phi: \mathcal{Z} \to T$ outputs an $\alpha$-approximate median of $\phi(s) \in T^m$ with probability at least $1-\beta$. The running time of the algorithm is $O(m \cdot \log|T|)$.

Proof: The algorithm is an instantiation of the exponential mechanism with the utility function $c: T \to \mathbb{R}$ defined as $$c_{\phi(s)}(v) \doteq \max\{|\{i \in [m]: \phi(s_i) < v\}|, |\{i \in [m]: \phi(s_i) > v\}|\}.$$

The algorithm outputs each $v \in T$ with probability $$Pr[M(s, \phi) = v] = \frac{\exp(\tfrac{-\varepsilon}{2} c_{\phi(s)}(v))}{\sum_{u \in T} \exp(\tfrac{-\varepsilon}{2} c_{\phi(s)}(u))}.$$

Since $c_{\phi(s)}(v)$ has sensitivity 1 as a function of s, this algorithm is $(\varepsilon, 0)$-differentially private (Theorem 3.1). Moreover, there is the accuracy guarantee (Corollary 3.12)

$$\forall s, \beta \Pr_{V \sim M(s,\phi)}\left[c_{\phi(s)}(V) < OPT_{\phi(s)} + \frac{2\ln(|T|/\beta)}{\varepsilon}\right] \geq 1-\beta, \quad (1)$$

where $OPT_{\phi(s)} \doteq \min_{u \in T} c_{\phi(s)}(u) \leq m/2$. Assuming the event in (1) happens for $V=v$ (that is, $$c_{\phi(s)}(v) < OPT_{\phi(s)} + \frac{2\ln(|T|/\beta)}{\varepsilon}\right),$$

so that $$\Pr_{Y \sim \phi(s)}[Y \leq v] = 1 - \frac{1}{m}|\{i \in [m]: \phi(s_i) > v\}| > \frac{1}{2} - \frac{2\ln(|T|/\beta)}{\varepsilon m} \geq \frac{1-\alpha}{2},$$

as long as $\alpha \geq 4 \ln(|T|/\beta)/\varepsilon m$, which is equivalent to $m \geq 4 \ln(|T|/\beta)/\varepsilon\alpha$. Similarly, the event in (1) implies that $$\Pr_{Y \sim \phi(s)}[Y < v] = \frac{1}{m}|\{i \in [m]: \phi(s_i) < v\}| < \frac{1}{2} + \frac{2\ln(|T|/\beta)}{\varepsilon m} \leq \frac{1+\alpha}{2}.$$

Thus, $$\Pr_{V \sim M(s,\phi)}\left[V \in qi_{\phi(s)}\left(\frac{1-\alpha}{2}, \frac{1+\alpha}{2}\right)\right] \geq 1-\beta$$

as long as $m \geq 4 \ln(|T|/\beta)/\varepsilon\alpha$.

To get an upper bound on the running time it is observed that using binary search, the elements of T can be split into m+1 "intervals" (that is contiguous subsets of T) with all elements of each interval having equal probability. This partition permits the computation of the normalization factor as well as the total probability of all the elements of T in each interval in $O(m \log|T|)$ time. A random point from the desired distribution can now be produced by first picking the interval proportionally to its probability and then outputting a point in that interval randomly and uniformly. (It is implicitly assumed that the structure of T is simple enough so that such operations can be performed in $O(\log|T|)$ time and ignore the time to evaluate $\phi$ on each of the elements of s.)

Another relatively simple and prior "folklore" algorithm will now be described finding an approximate median of a distribution that reduces the problem to $O(\log|T|)$ statistical queries. Recall, that an $\alpha$-accurate response to a statistical query $\psi: \mathcal{Z} \to [-1,1]$ relative to distribution $\mathcal{D}$ over $\mathcal{Z}$ is any value v such that $|v - \mathcal{D}[\psi]| \leq \alpha$.

Lemma 3.2: For all $\alpha>0$, finite $T \subset \mathbb{R}$, a query $\phi: \mathcal{Z} \to T$ and any distribution $\mathcal{D}$ over T, a value $$v \in qi_{\phi(\mathcal{D})}\left(\frac{1-\alpha}{2}, \frac{1+\alpha}{2}\right)$$

can be found using $\alpha/4$-accurate responses to at most $2\lceil \log_2(|T|) \rceil$ (adaptively-chosen) statistical queries relative to distribution $\mathcal{D}$.

Proof: Using binary search, a point $v \in T$ that satisfies the conditions $p_\leq(v) > \frac{1}{2} - \alpha/4$ and $p_<(v) < \frac{1}{2} + \alpha/4$, where $p_\leq(v)$ (or $p_<(v)$) is the response to the statistical query $\psi(z) = \mathbb{1}(v \leq \phi(z))(\psi(z) = \mathbb{1}(v < \phi(z))$, respectively). By the accuracy guarantees of the responses, $|p_\leq(v) - \Pr_{Z \sim \mathcal{D}}[\phi(Z) \leq v]| \leq \alpha/4$, and similarly for $p_<(v)$. The next point is chosen to test depending on which of the conditions fails (It can be assumed that $p_<(v) \leq p_\leq(v)$ so at most one condition can fail). Further, for the true median point of $\phi(\mathcal{D})$ (that is the point $v^* \in T$ for which $\Pr_{Z \sim \mathcal{D}}[\phi(Z) < v^*] < \frac{1}{2}$ and $\Pr_{Z \sim \mathcal{D}}[\phi(Z) \leq v^*] \geq \frac{1}{2}$) both conditions will be satisfied by the accuracy guarantees. Finally, by the accuracy guarantees, any point $v'$ that satisfies both of these conditions is an $\alpha$-approximate median for $\phi(\mathcal{D})$.

To find the $\alpha$-approximate median of values $\phi(s) \in T^m$ this reduction needs to be applied to the uniform distribution over the elements of $\phi(s)$. Answering statistical queries relative to this empirical distribution (commonly referred to as linear or counting queries) with differential privacy is a well-studied problem. For example, by using the standard Laplace or Gaussian noise addition algorithm one can obtain the following algorithm for finding an $\alpha$-approximate median.

Corollary 3.3: For all $\epsilon, \delta, \alpha, \beta \in (0, 1/2)$, finite $T \subset \mathbb{R}$ and all $$m \geq \frac{12\sqrt{2\lceil \log_2 |T| \rceil \cdot \ln\left(\frac{1}{\delta}\right) \cdot \ln\left(\frac{2\lceil \log_2 |T| \rceil}{\beta}\right)}}{\epsilon\alpha} = O\left(\frac{\sqrt{\log|T| \cdot \log\left(\frac{1}{\delta}\right) \cdot \log\left(\frac{\log|T|}{\beta}\right)}}{\epsilon\alpha}\right),$$

there exists an $(\epsilon, \delta)$-differentially private randomized algorithm M that given $s \in \mathcal{Z}^m$ and $\phi: \mathcal{Z} \to T$ outputs an $\alpha$-approximate median of $\phi(s)$ with probability at least $1-\beta$. The running time of the algorithm is $O(m \cdot \log|T|)$.

4. Generalization from Differential Privacy

In this section two proofs are provided that differential privacy gives generalization guarantees for statistical queries. The first proof—which may be called a strong generalization—is most similar to previous work, whereas the second proof—which may be called simple generalization—is much simpler, but gives a weaker bound that may only be suitable for estimators that are well-concentrated.

4.1 Strong Generalization

Theorem 4.1 in this subsection shows that any differentially private algorithm generalizes with high probability, with a small blowup in the allowed generalization error. This proof closely follows that of prior technique, but is quantitatively sharper. This quantitative sharpening allows estimation of the probability that a given value v is outside of $qi_{\phi(\mathcal{D})}(\rho, 1-\phi)$ with higher accuracy (that scales with $\rho$ as in the non-adaptive case). The sharper version in Section 5.1 is used; however, for results in this section $\rho = \frac{1}{4}$ and therefore the bounds from prior art approaches suffice.

The mean absolute deviation of a distribution $\mathcal{D}$ over $\mathbb{R}$ is defined as $$mad(\mathcal{D}) \perp \mathbb{E}_{Y' \sim \mathcal{D}}[|Y' - \mathbb{E}_{Y \sim \mathcal{D}}[Y]|].$$

Theorem 4.1: Fix $\alpha, \beta, \gamma \in (0,1)$ and $m, k \in \mathbb{N}$. Set $\epsilon = \frac{1}{2} \ln(1+\gamma)$ and $\delta = \alpha\beta/16$. Suppose $$m \geq \frac{8}{\epsilon\alpha} \ln(2k/\beta).$$

Let $M: \mathcal{Z}^m \to \mathcal{F}_{[0,1]}^k$ be a $(\epsilon, \delta)$-differentially private algorithm with $\mathcal{F}_{[0,1]}$ being the set of functions $\phi: \mathcal{Z} \to [0,1]$. Let $\mathcal{D}$ be a distribution on $\mathcal{Z}$. The $$\Pr_{\substack{S \sim \mathcal{D}^m \\ \phi_{[k]} \sim M(S)}}[\forall j \in [k]\ S[\phi_j] - \mathcal{D}[\phi_j] \leq \alpha + \gamma \cdot mad(\phi_j(\mathcal{D}))] \geq 1 - \beta.$$

Note that, by Jensen's inequality, $mad(\phi(\mathcal{D})) \leq sd(\phi(\mathcal{D}))$. Thus, Theorem 4.1 gives an error bound that scales with the standard deviation of the query (plus the absolute $\alpha$ term). Also, by the triangle inequality and the fact that $\phi(z) \geq 0$ for all z, it holds that $$mad(\phi(\mathcal{D})) \leq 2 \cdot \mathcal{D}[\phi].$$

Thus Theorem 4.1 can also be interpreted as giving a multiplicative accuracy guarantee (plus the additive $\alpha$). In comparison, the bound of prior techniques can be obtained (up to constants) by substituting the upper bound $mad(\phi(\mathcal{D})) \leq 1$ into Theorem 4.1. Thus, when $mad(\phi(\mathcal{D})) \ll 1$, the present bound is sharper.

As stated, Theorem 4.1 only applies in the non-adaptive setting and to statistical queries. However, this may be extended to prior monitoring techniques of and the cumulative probability function:

Theorem 4.2 Fix $\beta \in (0,1)$ and $k, m \in \mathbb{N}$ with $m \geq 2560 \ln(2k/\beta)$. Let M be an $(\frac{1}{20}, \beta/256)$-differentially private interactive algorithm that takes as input $s \in \mathcal{Z}^m$ and provides answers $v_1, \ldots, v_k \in \mathbb{R}$ to an adaptively-chosen sequence of queries $\phi_1, \ldots, \phi_k: \mathcal{Z} \to \mathbb{R}$. Suppose that, for all $s \in \mathcal{Z}^m$ and all interactive algorithms A, $$\Pr_{(\phi_{[k]}, v_{[k]}) \sim A \rightleftarrows M(S)}\left[\forall j \in [k] v_j \in qi_{\phi_j(s)}\left(\frac{3}{8}, \frac{5}{8}\right)\right] \geq 1 - \beta. \quad (3)$$

Then, for all distributions $\mathcal{D}$ and all interactive algorithm $$\Pr_{\substack{S \sim \mathcal{D}^m \\ (\phi_{[k]}, v_{[k]}) \sim A \rightleftarrows M(S)}}\left[\forall j \in [k] v_j \in qi_{\phi_j(\mathcal{D})}\left(\frac{1}{4}, \frac{3}{4}\right)\right] \geq 1 - 2\beta.$$

Proof: Let Q be the set of functions $\phi: \mathcal{Z} \to \mathbb{R}$ and let A be an arbitrary algorithm that asks queries in Q. Define $f: Q^k \times \mathbb{R}^k \to \mathcal{F}_{[0,1]}$ as follows, where $\mathcal{F}_{[0,1]}$ is the set of functions $\psi: \mathcal{Z} \to [0,1]$. Given $(\phi, v) \in Q^k \times \mathbb{R}^k$, define $\psi_1, \psi_{-1}, \psi_2, \psi_{-2}, \ldots, \psi_k, \psi_{-k}: \mathcal{Z} \to \{0,1\}$ by $\psi_j(x) \doteq \mathbb{1}(\phi_j(x) \leq v_j)$ and $\psi_{-j}(x) \doteq \mathbb{1}(\phi_j(x) \geq v_j)$ and let $$f(\phi, v) \doteq \underset{\psi \in \{\psi_1, \psi_{-1}, \psi_2, \psi_{-2}, \ldots, \psi_k, \psi_{-k}\}}{\operatorname{argmin}} \mathcal{D}[\psi].$$

By the post-processing property of differential privacy (Theorem 2.3), $f(A \leftrightarrows M(s))$ is a $(\varepsilon, \delta)$-differentially private algorithm (relative to its input $s \in \mathcal{Z}^m$). Moreover, by assumption (3), $$\forall s \in \mathcal{Z}^m \underset{\psi \sim f(A \rightleftarrows M(s))}{Pr}\left[s[\psi] \geq \frac{3}{8}\right] \geq 1 - \beta.$$

However, by Theorem 4.1, $$\underset{\substack{S \sim \mathcal{D}^m \\ \psi \sim f(A \rightleftarrows M(S))}}{Pr}\left[S[\psi] - \mathcal{D}[\psi] \leq \frac{1}{8}\right] \geq$$

$$\underset{\substack{S \sim \mathcal{D}^m \\ \psi \sim f(A \rightleftarrows M(S))}}{Pr}\left[S[\psi] - \mathcal{D}[\psi] \leq \frac{1}{16} + \frac{1}{8} \cdot \operatorname{mad}(\psi(\mathcal{D}))\right] \geq 1 - \beta.$$

Thus, by a union bound and the construction of f $$\underset{\substack{S \sim \mathcal{D}^m \\ (\phi_{[k]}, v_{[k]}) \sim A \rightleftarrows M(S)}}{Pr}\left[\forall j \in [k] v_j \in q i_{\phi_j(\mathcal{D})}\left(\frac{1}{4}, \frac{3}{4}\right)\right] =$$

$$\underset{\substack{S \sim \mathcal{D}^m \\ \psi \sim f(A \rightleftarrows M(S))}}{Pr}\left[\mathcal{D}[\psi] \geq \frac{1}{4}\right] \geq 1 - 2\beta.$$

Combining generalization (Theorem 4.2) with the present approximate median algorithm (Theorem 3.1) and composition (Theorem 2.4) yields the main result, Theorem 1.3. A somewhat more general statement that allows using different range $T_j$ for every query $\phi_j$ is thus proven. The same generalization applies to other results, but this is not stated for brevity.

Theorem 4.3: For any $\beta \in (0,1)$, $t, k, r \in \mathbb{N}$ and $\mathcal{Z} = X^t$, and with $$n \geq n_0 = O\left(t \sqrt{k \log\left(\frac{1}{\beta}\right)} \cdot \log\left(\frac{kr}{\beta}\right)\right)$$

there exists an interactive algorithm M that takes as input a dataset $s \in X^t$ and provides answers $v_1, \ldots, v_k \in \mathbb{R}$ to adaptively-chosen queries $(T_1, \phi_1), \ldots, (T_k, \phi_k)$, where for all $j \in [k]$, $|T_j| \leq r$ and $\phi_j: X^t \to T_j$ with the following accuracy guarantee. For all interactive algorithms A and distributions $\mathcal{P}$ on X, $$\underset{\substack{S \sim \mathcal{P}^n \\ (T_{[k]}, \phi_{[k]}, v_{[k]}) \sim A \rightleftarrows M(S)}}{Pr}\left[\forall j \in [k] v_j \in q i_{\phi_j(\mathcal{P}^t)}\left(\frac{1}{4}, \frac{3}{4}\right)\right] \geq 1 - \beta.$$

Proof The algorithm M promised by Theorem 4.3 is described below.

Input $S \in X^{mt}$.
Partition S into $S_1, \ldots, S_m \in X^t$
For $j=1, 2, \ldots, k$:
    Receive a set $T_j$ and a query $\phi_j: X^t \to T_j$.
    Run the $(\tilde{\varepsilon}, 0)$-differentially private ¼-approximate median algorithm $\tilde{M}$ from
    Thm. 3.1 for $T_j$ and with inputs $(S_1, \ldots, S_m)$ and $\phi_j$ to obtain output $v_j \in T_j$.
    Return answer $v_j$.

Let $\mathcal{Z} \doteq X^t$ and assume that for some r fixed in advance, $r \geq \max_{j \in [K]}|T_j|$. Theorem 3.1 says that if $m \geq 4 \ln(kr/\beta)/(\alpha \tilde{\varepsilon})$, then each execution of the median algorithm is $(\tilde{\varepsilon}, 0)$-differentially private and outputs an $\alpha$-approximate median with probability at least $1-\beta/k$. Here $\alpha=\frac{1}{4}$, so this rearranges to $\tilde{\varepsilon}=16 \ln(kr/\beta)/m$. This implies that for all interactive algorithms A and every $s \in \mathcal{Z}^m$ $$\underset{(T_{[k]}, \phi_{[k]}, v_{[k]}) \sim A \rightleftarrows M(S)}{Pr}\left[\forall j \in [k] v_j \in q i_{\phi_j(d)}\left(\frac{3}{8}, \frac{5}{8}\right)\right] \geq 1 - \beta. \quad (4)$$

Interactive composition (Theorem 2.5 implies that M is $(\varepsilon, \delta)$-differentially private for any $\delta \in (0,1)$ and $$\varepsilon = \frac{k}{2}\left(\frac{16\ln(kr/\beta)}{m}\right)^2 + \frac{16\ln(kr/\beta)}{m}\sqrt{2k\ln(1/\delta)}. \quad (5)$$

By Theorem 4.2, if, in addition to (4), it is had that $\varepsilon < \frac{1}{20}$ for $\delta = \beta/256$ in (5) and $m \geq 2560 \ln(2k/\beta)$, then, for all distributions $\mathcal{P}, \mathcal{D} \doteq \mathcal{P}^t$ and all interactive algorithms A, $$\underset{\substack{S \sim \mathcal{D}^m \\ (T_{[k]}, \phi_{[k]}, v_{[k]}) \sim A \rightleftarrows M(S)}}{Pr}\left[\forall j \in [k] v_j \in q i_{\phi_j(\mathcal{D})}\left(\frac{1}{4}, \frac{3}{4}\right)\right] \geq 1 - 2\beta,$$

which is the desired conclusion.

It only remains to find the appropriate bound on the parameter m. $m \geq 2560 \ln(2k/\beta)$ and $$\frac{1}{20} \geq \varepsilon = \frac{k}{2}\left(\frac{16\ln\left(\frac{kr}{\beta}\right)}{m}\right)^2 + \frac{16\ln\left(\frac{kr}{\beta}\right)}{m}\sqrt{2k\ln\left(\frac{256}{\beta}\right)}.$$

Setting $m=640\sqrt{\max\{k,16\} \cdot \ln(256/\beta)} \cdot \ln(kr/\beta)$ achieves this.

A relatively simple corollary of Theorem 4.3 is now described that converts the (¼, ¾)-quantile interval guarantees to explicit additive error guarantees. The error will be measured in terms of the mean absolute deviation of the query $\phi$ on inputs sampled from $\mathcal{P}^t$ (eq. 2). For normalization purposes it is also assumed that queries are scaled by the analyst is such a way that both $\mathcal{P}^t[\phi] \in [-1,1]$ and $\operatorname{mad}(\phi(\mathcal{P}^t)) \leq 1$. Note that this assumption is implied by $\phi$ having range $[-1,1]$ and, in general, allows $\phi$ to have an infinite range.

Corollary 4.4: For $t \in \mathbb{N}$ and a distribution $\mathcal{P}$ over X, let $\mathcal{F}_{\mathcal{P},t}$ denote the set of functions $\phi: X^t \to \mathbb{R}$ such that $\mathcal{P}^t[\phi] \in [-1,1]$ and $\operatorname{mad}(\phi(\mathcal{P}^t)) \leq 1$. For all $\zeta > 0$, $\beta > 0$, $k \in \mathbb{N}$, and $n \geq n_0 = O(t\sqrt{k \log(1/\beta)} \cdot \log(k/(\zeta\beta)))$, there exists an efficient algorithm M which takes a dataset $s \in X^n$ as an input and provides answers $v_1, \ldots, v_k \in \mathbb{R}$ to an adaptively-chosen sequence of queries $\phi_1, \ldots, \phi_k: X^t \to \mathbb{R}$ satisfying: for all interactive algorithms A and distributions $\mathcal{P}$ over X $$\Pr_{\substack{S \sim \mathcal{P}^n \\ (\phi_{[k]}, v_{[k]}) \sim A \leftrightarrows M(S)}} [\forall\, j \in [k] \text{ s.t. } \phi_j \in \mathcal{F}_{\mathcal{P}, t}: |v_j - \mathcal{P}^t[\phi_j]| \le 4 \cdot (\phi_j(\mathcal{P}^t)) + \zeta] \ge 1 - \beta.$$

Proof It should first be observed that by Markov's inequality, $$\Pr_{Z \sim \mathcal{P}_t}[|\phi(Z) - \mathcal{P}^t[\phi]| \ge 4 \cdot mad(\phi(\mathcal{P}^t))] \le \frac{1}{4}.$$

Therefore, $$qi_{\phi(\mathcal{P}^t)}\left(\frac{1}{4}, \frac{3}{4}\right) \subseteq [\mathcal{P}^t[\phi] - 4 \cdot \text{mad}(\phi(\mathcal{P}^t)), \mathcal{P}^t[\phi] + 4 \cdot \text{mad}(\phi(\mathcal{P}^t))].$$

Hence for all $j \in [k]$ such that $\varphi_j \in \mathcal{F}_{\mathcal{P},t}$ $qi_{\phi_j(\mathcal{P}^t)}$ $(\frac{1}{4}, \frac{3}{4}) \subseteq [-5, 5]$. Now T is defined to be the interval $[-5,5]$ discretized with step $\zeta$, or $T = \{r \cdot \zeta : r \in \mathbb{Z}\} \cap [-5,5]$. To answer a query $\phi_j$ define $\phi'_j: X^t \to T$ as $\phi'_j(z) = \operatorname{argmin}_{v \in T} |v - \phi_j(z)|$ and then use the algorithm from Theorem 4.3 to answer the query $\phi'_j$. The projection of the values of $\phi$ to T simultaneously truncates the range to $[-5,5]$ and discretizes it. The $(\frac{1}{4}, \frac{3}{4})$-quantile interval of $\varphi_j(\mathcal{P}^t)$ is inside the interval $[-5,5]$ and therefore is not affected by the truncation step. The discretization can affect this interval by at most $\zeta$. Combining this with (6) it is obtained that if $\phi_j \in \mathcal{F}_{\mathcal{P},t}$ then $$qi_{\phi'_j(\mathcal{P}^t)}\left(\frac{1}{4}, \frac{3}{4}\right) \subseteq [\mathcal{P}^t[\phi_j] - 4 \cdot \text{mad}(\phi_j(\mathcal{P}^t)) - \zeta,$$

$$\mathcal{P}^t[\phi_j] + 4 \cdot \text{mad}(\phi_j(\mathcal{P}^t)) + \zeta].$$

Therefore the value $v_j$ returned by the algorithm from Theorem 4.3 to query $\phi'_j$ satisfies:

$$|v_j - \mathcal{P}^t[\phi_j]| \le 4 \cdot mad(\phi_j(\mathcal{P}^t)) + \zeta.$$

Now to obtain the claimed bound on the sample complexity it is observed that $|T| \le 10/\zeta$.

Remark 1: Note that mean absolute deviation of $\phi$ is upper-bounded by the standard deviation of $\phi$. Therefore Corollary 4.4 also holds with $\text{mad}(\phi_j(\mathcal{P}^t))$ replaced by sd $(\phi_j(\mathcal{P}^t))$ both in the definition of $\mathcal{F}_{t,\mathcal{P}}$ and the accuracy bound (with the constant factor 4 being replaced by 2 since Chebyshev's inequality can be used instead of Markov's). The obtained statement generalizes Theorem 1.2 described. The quantile-based guarantees of the other algorithms can be converted to additive error guarantees in an analogous way.

Somewhat sharper (asymptotic) bounds can be obtained by using the approximate median algorithm based on linear queries (Lemma 3.2) together with the algorithm for answering linear queries in prior techniques. Specifically, this algorithm can solve the problem given $n = O(t \sqrt{k \cdot \log(1/\zeta) \cdot \log(1/\beta) \cdot \log(\log(k \log(1/\zeta))/\beta)}$ samples.

4.2 Simple Generalization

A relatively simple and seemingly weak generalization result that shows the output of a differentially private algorithm cannot "overfit" its input dataset will now be described. Namely, if an $(\varepsilon, \delta)$ differentially private algorithm outputs a function $\phi: \mathcal{Z} \to \mathbb{R}$ on a dataset $s \in \mathcal{Z}^m$ sampled from $\mathcal{D}^m$, then the value of $\phi$ on any element of the dataset is within the $(\rho, 1-\phi)$-quantile interval of $\phi(\mathcal{D})$ with probability at least $1-(2e^\varepsilon \rho + \delta)$. To obtain meaningful guarantees about the whole dataset from such generalization result, p must be relatively small (much smaller than the desired $\frac{1}{4}$). The good news is that for an estimator that is well-concentrated around its mean, even values within $(\rho, 1-\phi)$-quantile interval for small p are close to the mean. Note that, in principle, any estimator can be amplified by sampling and taking a median before being used in this analysis and hence generalization guarantees can be obtained from such relatively simple analysis even in the general case (although the algorithm in this case would need to use two median steps).

Theorem 4.5 Let $M: \mathcal{Z}^m \to \mathcal{F}_{[0,1]}$ be a $(\varepsilon, \delta)$-differentially private algorithm with $\mathcal{F}_{[0,1]}$ being the set of functions $\phi: \mathcal{Z} \to [0,1]$. Let $\mathcal{D}$ be a distribution on $\mathcal{Z}$. Then for all $i \in [m]$, $$\Pr_{\substack{S \sim \mathcal{D}^m \\ \phi \sim M(S)}} [\phi(S_i) \notin qi_{\phi(\mathcal{D})}(\rho, 1-\rho)] \le 2\rho e^\varepsilon + \delta$$

By differential privacy, for all $i \in [m]$ $$\Pr_{\substack{S \sim \mathcal{D}^m \\ \phi \sim M(S)}} [\phi(S_i) \notin qi_{\phi(\mathcal{D})}(\rho, 1-\rho)] \le e^\varepsilon \Pr_{\substack{(S,Z) \sim \mathcal{D}^m \times \mathcal{D} \\ \phi \sim M(S_{-i}, Z)}} [\phi(S_i) \notin qi_{\phi(\mathcal{D})}(\rho, 1-\rho)] +$$

$$= e^\varepsilon \Pr_{\substack{(S,Z) \sim \mathcal{D}^m \times \mathcal{D} \\ \phi \sim M(S)}} [\phi(Z) \notin qi_{\phi(\mathcal{D})}(\rho, 1-\rho)] +$$

$$\le e^\varepsilon 2\rho + \delta,$$

where the equalities follow from the fact that the pairs $(S, Z)$ and $((S_{-i}, Z), Z_i)$ are identically distributed and the definition of the $(\rho, 1-\phi)$-quantile interval.

Now for $\rho$ and $\delta$ that are sufficiently small, Theorem 4.5 ensures that with probability at least $1-\beta$, for all $i \in [m]$, $\varphi(s_i) \in qi_{\phi(\mathcal{D})}(\rho, 1-\phi)$. This means that to get a value in $qi_{\phi(\mathcal{D})}(\rho, 1-\phi)$, an algorithm that outputs a value that is in between the smallest and the largest values of $\phi$ on the elements of a dataset s may be used. Such value is referred to as an interior point of $\phi(s)$ (and is equivalent to a 1-approximate median). This argument gives the following theorem.

Theorem 4.6: For any $\beta \in (0,1)$, $t, k \in \mathbb{N}$, a finite set $T \subset \mathbb{R}$ and $\mathcal{Z} = X^t$, and with $$n \ge n_0 = O\left(t \cdot \sqrt{k} \cdot \log\left(\frac{|T|}{\beta}\right) \cdot \log^{\frac{1}{2}}\left(\frac{k \log(|T|)}{\beta}\right)\right)$$

there exists an interactive algorithm M that takes as input a dataset $s \in X^n$ and provides answers $v_1, \ldots, v_k \in T$ to adaptively-chosen queries $\phi_1, \ldots, \phi_k: X^t \to T$ such that, for all interactive algorithms A and distributions $\mathcal{P}$ on X, $$\Pr_{\substack{S \sim \mathcal{P}^n \\ (\phi_{[k]}, v_{[k]}) \sim A \leftrightarrows M(S)}} [\forall\, j \in [k]\, v_j \in qi_{\phi_j(\mathcal{P}^t)}(\rho, 1-\rho)] \ge 1 - \beta,$$

where $\rho = \beta \cdot \dfrac{t}{4kn} = \tilde{\Omega}\left(\dfrac{\beta}{k^{\frac{3}{2}} \cdot \log|T|}\right)$.

The algorithm for answering adaptive queries above is used, but with 1-approximate median, instead of $\frac{1}{4}$. As in the proof of Theorem 1.3, $\mathcal{Z} = X^t$ and $\mathcal{D} = \mathcal{P}^t$. Theorem 3.1 says that if $m \geq 4 \ln(2k|T|/\beta)/\tilde{\epsilon}$, then each execution of the median algorithm is $(\tilde{\epsilon}, 0)$-differentially private for every input query $\phi_j: Z \to T_j$. This implies that for all interactive algorithms A and every $s \in Z^m$, $$\Pr_{(\phi_{[k]}, v_{[k]}) \sim A \rightleftarrows M(s)} [\forall j \in [k] \ v_j \in qi_{\phi_j(s)}(0, 1)] \geq 1 - \frac{\beta}{2}. \quad (7)$$

The interactive composition (Theorem 2.5) implies that M is $(\epsilon, \delta)$-differentially private for any $\delta \in (0,1)$ and $$\epsilon = \frac{k}{2}\left(\frac{4\ln\left(\frac{2|T|}{\beta}\right)}{m}\right) + \frac{4\ln\left(\frac{2|T|}{\beta}\right)}{m}\sqrt{2k\ln\left(\frac{1}{\delta}\right)}.$$

Now applying Theorem 4.5 and a union bound:

$$\Pr_{\substack{S \sim \mathcal{D}^m \\ (\phi_{[k]}, v_{[k]}) \sim A \rightleftarrows M(S)}} [\exists j \in [k], i \in [m] \ \phi_j(S_i) \notin qi_{\phi_j(\mathcal{D})}(\rho, 1-\rho)] \leq$$

$$km(e^{\epsilon}2\rho + \delta).$$

Combining this with (7):

$$\Pr_{\substack{S \sim \mathcal{D}^m \\ (\phi_{[k]}, v_{[k]}) \sim A \rightleftarrows M(S)}} [\forall j \in [k] \ v_j \in qi_{\phi_j(\mathcal{D})}(\rho, 1-\rho)] \geq 1 - \frac{\beta}{2} - km(e^{\epsilon}2\rho + \delta).$$

Setting $m = 8 \log(2|T|/\beta)\sqrt{2k\ln(1/\delta)}$ ensures that $\sqrt{\epsilon} \leq \ln 2$. Hence for $\delta = \beta/(10 \ km)$ and $\rho = \beta/(10 \ km)$ it is obtained that $km(e^{\epsilon}2\rho+\delta) \leq \beta/2$.

For example, if each $\phi_j$ is $(1/\sqrt{t})$-subgaussian with the mean $\mathcal{P}'[\phi_j] \in [-1, 1]$ then for every $\alpha > 0$, setting $t = \tilde{O}(\log(k/\beta)/\alpha^2)$ ensures that $qi_{\phi_j(\mathcal{P}^t)}(\rho, 1-\rho) \subseteq [\mathcal{P}'[\phi_j] - \alpha, \mathcal{P}'[\phi_j] + \alpha]$. This implies that the means can be estimated with accuracy $\alpha$ given $\tilde{O}(\sqrt{k} \cdot \log^2(1/\beta)/\alpha^2)$ samples. Note that low-sensitivity queries are $(1/\sqrt{t})$-subgaussian and therefore the sample complexity of the present algorithm given by this simple analysis is comparable to the best known for this problem.

As pointed out above, this analysis can also be used to deal with general estimators by adding an additional amplification step. Namely, computing the estimator on several independent subsamples and taking (the exact) median. The resulting algorithm would have sample complexity that is identical to that obtained in Theorem 4.3 up to an additional logarithmic factor (which can be removed with careful calibration of parameters).

5. Dealing with a Large Number of Queries

In this section ways to use the approach described herein when the number of queries that needs to be answered is (relatively) large are described. Namely, an algorithm for answering verification queries and an algorithm whose complexity scales as $\log k$, rather than $\sqrt{k}$ is provided.

5.1 Verification Queries

Another application of techniques from differential privacy given by prior art techniques is an algorithm that given a statistical query and a proposed estimate of the expectation of this query, verifies the estimate. This problem requires less data if most proposed answers are correct. Specifically, the number of samples needed by this algorithm is (just) logarithmic in the number of queries k but also scales linearly in $\sqrt{l}$, where l is the number of queries that fail the verification step. This result is extended to low-sensitivity queries using these results also based upon prior art techniques. In addition, prior art techniques describe a query verification algorithm that can handle arbitrary queries (not just real-valued), which however has sample complexity with linear dependence on l. Its analysis is based on a simple description length-based argument.

A natural way to apply such algorithms is the reusable holdout technique. In this technique the dataset is split into two disjoint parts: the "training" set $s_t$ and the holdout set $s_h$. The analyst then uses the training set to answer queries and perform other arbitrary analyses. The holdout set is used solely to check whether the answers that were obtained on the training set generalize. Another application is an algorithm referred to as Effective Rounds. This algorithm splits the dataset into several disjoint subsets and at each time uses only one of the subsets to answer queries. An algorithm for verifying answers to queries is used to switch to a new subset of samples whenever a query fails the verification step (and uses its own subset of samples).

Here, an algorithm for verifying answers to queries about general estimators is described. Formally, the algorithm satisfies the following guarantees.

Theorem 5.1 Fix $\rho > \alpha > 0$, $\beta > 0$, $l$, $t$, $k \in \mathbb{N}$, and $n \geq n_0 = O(t\sqrt{l\log(1/\alpha\beta)} \log(k/\beta)\rho/\alpha^2)$. There exists an interactive algorithm M that takes as input $s \in X^n$ and provides answers $a_1, \ldots, a_k \in \{Y, N, \perp\}$ to adaptively-chosen queries $(\phi_1, v_1), \ldots, (\phi_k, v_k)$ (where $\phi_j: X^t \to \mathbb{R}$ and $v_j \in \mathbb{R}$ for all $j \in [k]$) satisfying the following: for all interactive algorithms A and distributions $\mathcal{P}$ over X, $$\Pr_{\substack{S \sim \mathcal{P}^n \\ (\phi_{[k]}, v_{[k]}) \sim A \rightleftarrows M(S)}}\left[\forall j \in [k] \begin{array}{l} v_j \in qi_{\phi_j(\mathcal{P}^t)}(\rho, 1-\rho) \Longrightarrow a_j \in \{Y, \perp\} \\ v_j \notin qi_{\phi_j(\mathcal{P}^t)}(\rho-\alpha, 1-\rho+\alpha) \Longrightarrow a_j \in \{N, \perp\} \\ |\{j' \in [j-1]: a_{j'} = N\}| = \ell \iff a_j = \perp \end{array}\right] \geq 1 - \beta.$$

First, the accuracy promise of this algorithm is described. Each query is specified by a function $\phi_j: X^t \to \mathbb{R}$ as well as a "guess" $v_j \in \mathbb{R}$. The guess is "good" if $v_j \in qi_{\phi_j(\mathcal{P}^t)}(\rho, 1-\rho)$ and "bad" if $v_j \in qi_{\phi_j(\mathcal{P}^t)}(\rho-\alpha, 1-\rho+\alpha)$. Essentially, the guarantee is that, if the guess is good, the algorithm answers Y and, if the guess is bad, the algorithm answers N. However, there are two caveats to this guarantee—(i) if the guess is neither good nor bad, then the algorithm may output either Y or N and, —(ii) once the algorithm has given the answer N to l queries, its failure budget is "exhausted" and it only outputs $\perp$.

Note that this algorithm handles only the verification and does not provide correct answers to queries that failed the verification step. To obtain correct responses one can run an instance of the query-answering algorithm from Theorem 1.3 in parallel with the verification algorithm. The query-answering algorithm would be used only l times and hence the dataset size it would require would be independent of k and scale linearly in $\sqrt{l}$. (The two algorithms can either be run on disjoint subsets of data or on the same dataset since differential privacy composes.)

The proof is a reduction of the verification step to verification of answers to statistical queries (relative to $\mathcal{P}^t$).

Hence the results may be directed applied from prior approaches to analyze the present algorithm. However, as mentioned above, for small values of ρ, the existing algorithm has suboptimal dependence of sample complexity on ρ and α. Specifically, the dependence is $1/\alpha^2$ instead of $\rho/\alpha^2$ which, in particular, is quadratically worse for the typical setting of $\alpha=\Theta(\rho)$. Note that the dataset size grows with l—the number of times that "No" is returned to a verification query. Therefore choosing a small ρ is useful for ensuring that "No" is returned only when overfitting is substantial enough to require correction.

To improve this dependence the sharper generalization result is used (Theorem 4.2). But first, the stability properties of the sparse vector technique that are the basis of this algorithm.

Theorem 5.2 For all α, β, ε, δ>0, m, k, l∈ℕ with $$m \geq m_0 = O\left(\frac{\sqrt{\ell \log\left(\frac{1}{\delta}\right)} \log\left(\frac{k}{\beta}\right)}{\varepsilon \alpha}\right),$$

there exists an interactive (ε, δ)-differentially private algorithm $\tilde{M}$ that takes as input $s \in \mathcal{Z}^m$ and provides answers $b_1, \ldots, b_k \in \{Y, N, \perp\}$ to adaptively chosen queries $(\psi_1, u_1), \ldots, (\psi_k, u_k)$ (where $\psi_j: \mathcal{Z} \to \mathbb{R}$ and $u_j \in \mathbb{R}$ for all $j \in [k]$) with the following accuracy guarantee. For all interactive algorithms A and all $s \in \mathcal{Z}^m$ $$\Pr_{(\psi_{[k]}, u_{[k]}, b_{[k]}) \sim A \leftrightarrows \tilde{M}(s)} \left[ \forall j \in [k] \begin{array}{l} s[\psi_j] > u_j \implies b_j \in \{Y, \perp\} \\ s[\psi_j] \leq u_j - \alpha \implies b_j \in \{N, \perp\} \\ |\{j' \in [j-1] : b_{j'} = N\}| = \ell \iff b_j = \perp \end{array} \right] \geq 1 - \beta.$$

Proof [of Theorem 5.1]: As before, $\mathcal{Z} \doteq X^t$, $\mathcal{D} \doteq \mathcal{P}^t$ and the input dataset is viewed as an element of $\mathcal{Z}^m$ sampled from $\mathcal{D}^m$.

The sparse vector algorithm of Theorem 5.2 is used. Theorem 4.1 is used to convert the empirical guarantee into a guarantee relative to the data distribution, as in Theorem 4.2. However, every verification query is converted into two statistical queries to check the two "ends" of the quantile interval. That is, given a verification query $(\phi_j, v_j)$ for which it is desirable to know whether $v_j \in q_{l_{\phi_j(\mathcal{D})}}(\rho, 1-\rho)$ or $v_j \in q_{l_{\phi_j(\mathcal{D})}}(\Sigma-\alpha, 1-\rho+\alpha)$, two statistical queries $\psi_{2j-1}$ and $\psi_{2j}$ are presented for which it is desirable to know if $\mathcal{D}[\phi] > \rho$ or $D[\psi] < \rho - \alpha$ (with $\psi \in \{\psi_{2j-1}, \psi_{2j}\}$). Formally, there is the following reduction.

The sparse vector algorithm $\tilde{M}$ of Theorem 5.2 is converted into an algorithm M of the desired form of Theorem 5.1: Each query $(\phi_j, v_j)$ to M is converted into two queries $(\psi_{2j-1}, u_{2j-1})$ and $(\psi_{2j}, u_{2j})$ to $\tilde{M}$, where $$\psi_{2j-1}(z) = 1(\phi_j(x) \leq v_j), \psi_{2j-1}(z) = 1(\phi_j(x) \geq v_j), u_{2j-1} = u_{2j} = \rho - \frac{\alpha}{3}.$$

These queries have the following key property: (†) If $v_j \in q_{l_{\phi_j(\mathcal{D})}}(\rho, 1-\rho)$, then $\mathcal{D}[\psi_{2j-1}] > \rho$ and $\mathcal{D}[\psi_{2j}] > \rho$. If $v_j \in q_{l_{\phi_j(\mathcal{P}^t)}}(\rho-\alpha, 1-\rho+\alpha)$, then either $\mathcal{D}[\psi_{2j-1}] \leq \rho - \alpha$ or $\mathcal{D}[\psi_{2j}] \leq \rho - \alpha$ (but not both). Let $b_{2j-1}$ and $b_{2j}$ be the answers produced by $\tilde{M}$ to $(\psi_{2j-1}, u_{2j-1})$ and $(\psi_{2j}, u_{2j})$ respectively. If $b_{2j-1} = b_{2j} = Y$, then M returns $a_j = Y$. If $b_{2j-1} = \perp$ or $b_{2j} = \perp$ (or both), then M returns $a_j = \perp$. Otherwise M returns $a_j = N$.

Note that $\tilde{M}$ must answer twice as many queries as M; thus $\tilde{M}$ must be instantiated with the value k being twice as large as for M. $\tilde{M}$ is also instantiated with a reduced by a factor of 3 and β reduced by a factor of 2. The values ε and δ used by $\tilde{M}$ will be determined later in this proof.

In particular, $\tilde{M}$ is instantiated to achieve the following accuracy guarantee. For all interactive algorithms A and all $s \in \mathcal{Z}^m$ $$\Pr_{(\psi_{[k]}, u_{[k]}, b_{[k]}) \sim A \leftrightarrows \tilde{M}(s)} \left[ \forall j \in [k] \begin{array}{l} s[\psi_j] > u_j \implies b_j \in \{Y, \perp\} \\ s[\psi_j] \leq u_j - \alpha/3 \implies b_j \in \{N, \perp\} \\ |\{j' \in [j-1] : b_{j'} = N\}| = \ell \iff b_j = \perp \end{array} \right] \geq 1 - \frac{\beta}{2}.$$

Now is will be shown that M satisfies the promised accuracy requirement relative to the distribution $\mathcal{D}$ rather than relative to the empirical values. Given the key property (†) above, it suffices to show that, with probability at least $1-\beta/2$ over a random choice of $S \sim \mathcal{D}^m$, for all $j \in [2k]$ and $(\psi_{[k]}, u_{[k]}, b_{[k]}) \sim A \leftrightarrows \tilde{M}(S)$, so that $$\mathcal{D}[\psi_j] \geq \rho \implies S[\psi_j] > u_j = \rho - \alpha/3 \text{ and } \mathcal{D}[\psi_j] \leq \rho - \alpha \implies S[\psi_j] \leq u_j - \alpha/3 = \rho - 2\alpha/3. \quad (8)$$

Furthermore, to prove (8), it suffices to have $$\mathcal{D}[\psi_j] \cdot \frac{\rho - \frac{\alpha}{4}}{\rho} - \frac{\alpha}{12} \leq S[\psi_j] \leq \mathcal{D}[\psi_j] \cdot \frac{\rho - \frac{3\alpha}{4}}{\rho - \alpha} + \frac{\alpha}{12},$$

which is, in turn, implied by $$|S[\psi_j] - \mathcal{D}[\psi_j]| \leq \frac{\alpha}{4\rho} \cdot \mathcal{D}[\psi_j] + \frac{\alpha}{12}.$$

Theorem 4.1 is now used to prove that (9) holds simultaneously for all $j \in [2k]$ with probability at least $1-\beta/2$, as required to complete the proof. First, define $f: \mathcal{F}_{\{0,1\}}^{2k} \times \mathbb{R}^{2k} \times \{Y, N, \perp\}^{2k} \to \mathcal{F}_{\{0,1\}}^{4k}$ by $f(\psi, u, b) = (\psi_1, 1-\psi_1, \psi_2, 1-\psi_2, \ldots, \psi_{2k}, 1-\psi_{2k})$. By post-processing (Theorem 2.3), $f(A \leftrightarrows \tilde{M}(s))$, is an (ε, δ)-differentially private function of $s \in \mathcal{Z}^m$ for all interactive algorithms A. The output of $f(A \leftrightarrows M(s))$, is 4k functions mapping $\mathcal{Z}$ to $\{0,1\}$. Set $$\varepsilon = \frac{1}{2} \ln\left(1 + \frac{\alpha}{8\rho}\right)$$

and $\delta = \alpha \beta / (16 \cdot 2 \cdot 12)$.
Suppose $$m \geq \frac{8 \cdot 12}{\varepsilon \alpha} \ln(16k/\beta).$$

By theorem 4.1, $$\Pr_{\substack{S\sim \mathcal{D}^m \\ \hat{\psi}\sim f(A\rightleftarrows M(S))}}\left[\forall\, j\in[2k]\quad\begin{array}{c}S[\psi_j]-\mathcal{D}[\psi_j]\le \frac{\alpha}{12}+\frac{\alpha}{S_\rho}\cdot\mathrm{mad}(\psi_j(\mathcal{D}))\\ S[1-\psi_j]-\mathcal{D}[1-\psi_j]\le \frac{\alpha}{12}+\frac{\alpha}{8_\rho}\cdot\mathrm{mad}(\psi_j(\mathcal{D}))\end{array}\right]\ge 1-\frac{\beta}{2}. \quad (10)$$

Note that $\max\{S[\psi_j]-\mathcal{D}[\psi_j],\ S[1-\psi_j]-\mathcal{D}[1-\psi_j]\}=|S[\psi_j]-\mathcal{D}[\psi_j]|$ and mad of $\psi_j$ is equal to mad of $1-\psi_j$. Since $\mathrm{mad}(\psi_j(D))\le 2\cdot \mathcal{D}[\psi_j]$, the generalization bound (10) implies the desired bound (9) holds simultaneously for all $j\in[2k]$ with probability at least $1-\beta/2$, as required.

It only remains to work out the parameters. Thus, $\varepsilon\ge\alpha/18\rho$. Theorem 4.1 requires $m\ge m_1$ where $$m_1 = \frac{8\cdot 12}{\varepsilon\alpha}\ln(16k/\beta) \le 8\cdot 12\cdot 18\frac{\rho}{\alpha^2}\ln(16k/\beta),$$

while Theorem 5.2 requires $$m\ge m_0 = O\left(\frac{\sqrt{t\log\left(\frac{1}{\delta}\right)}\log\left(\frac{k}{\beta}\right)}{\varepsilon\alpha}\right) = O\left(\frac{\sqrt{t\log\left(\frac{1}{\alpha\beta}\right)}\log\left(\frac{k}{\beta}\right)\rho}{\alpha^2}\right).$$

Thus the final sample complexity is $\max\{m_0, m_1\}$, as required.

5.2 Private Multiplicative Weights

A result in which the dependence of the required dataset size on the number of queries k is logarithmic (at the expense of some additional terms and computational efficiency) is now described. It is known that in this general setting, the dependence on the data universe size and the loss of computational efficiency are unavoidable.

The present result follows from a direct combination of an algorithm for answering statistical queries and the reduction from the approximate median problem to the problem of answering statistical queries relative to distribution $\mathcal{D}=\mathcal{P}^t$ (given in Lemma 3.2). Specifically, the following result that is based on the private multiplicative weights algorithm of prior approaches.

Theorem 5.3 For all $\alpha, \beta\in(0,1)$ and m, $k\in\mathbb{N}$ with $$m\ge m_0 = O\left(\sqrt{\log|\mathcal{Z}|}\cdot\log k\cdot\frac{\log^{\frac{3}{2}}\left(\frac{1}{\alpha\beta}\right)}{\alpha^3}\right),$$

there exists an interactive algorithm M that takes as input a dataset $s\in\mathcal{Z}^m$ and provides answers $v_1, \ldots, v_k\in[-1,1]$ to adaptively-chosen queries $\psi_1, \ldots, \psi_k:\mathcal{Z}\to[-1,1]$ such that, for all interactive algorithms A and distributions $\mathcal{D}$ over $\mathcal{Z}$, $$\Pr_{\substack{S\sim\mathcal{D}^m \\ (\psi_{[k]},v_{[k]})\sim A\rightleftarrows M(s)}}[\forall\, j\in[k]\mid v_j-\mathcal{D}[\psi_j(\mathcal{D})]\le\alpha]\ge 1-\beta.$$

Now, by Lemma 3.2, for $\mathcal{Z}=X^t$ and $\mathcal{D}=\mathcal{P}^t$ and any query $\phi:\mathcal{Z}\to T$, responses to $2\lfloor\log_2|T|\rfloor$ statistical queries relative to $\mathcal{D}$ with accuracy $\frac{1}{8}$ can be used to find a value $v\in qi_{\phi(\mathcal{D})}(\frac{1}{4},\frac{3}{4})$. By plugging this reduction into Theorem 5.3 the following result is obtained Theorem 5.4 For any $\beta\in(0,1)$, t, $k\in\mathbb{N}$, a finite set $T\subseteq\mathbb{R}$ and $\mathcal{Z}=X^t$ and with $$n\ge n_0 = O\left(t^{\frac{3}{2}}\cdot\sqrt{\log|X|}\cdot\log(k\log|T|)\cdot\log^{\frac{3}{2}}\left(\frac{1}{\beta}\right)\right)$$

there exists an interactive algorithm M that takes as input a dataset $s\in\mathcal{P}^n$ and provides answers $v_1, \ldots, v_k\in T$ to adaptively-chosen queries $\phi_1, \ldots, \phi_k:X^t\to T$ such that, for all interactive algorithms A and distributions $\mathcal{P}$ over X, $$\Pr_{\substack{S\sim\mathcal{P}^m \\ (\phi_{[k]},v_{[k]})\sim A\rightleftarrows M(S)}}\left[\forall\, j\in[k]v_j\in qi_{\phi_j(\mathcal{P}^t)}\left(\frac{1}{4},\frac{3}{4}\right)\right]\ge 1-\beta.$$

For example, this algorithm may be used to obtain a new algorithm for answering a large number of low-sensitivity queries (that is queries $\phi:X^t\to[-1,1]$ such that $\Delta(\phi)=1/t$). To answer queries with accuracy $\alpha$ $t=16/\alpha^2$ can be used and set T that is the interval $[-1,1]$ discretized with step $\alpha/2$. Thus the number of samples that the present algorithm uses is $n=O(\sqrt{\log|X|}\cdot\log(k/\alpha)\cdot\log^{3/2}(1/\beta)/\alpha^3)$. For comparison, the best previously known algorithm for this problem uses $$n = O\left(\log|X|\cdot\log\left(\frac{k}{\alpha}\right)\cdot\frac{\log^{\frac{3}{2}}\left(\frac{1}{\beta}\right)}{\alpha^4}\right)$$

Although, as pointed out herein, the setting in which each query is applied to the entire dataset is more general than the present dataset.

The present invention may be a system, a method, and/or a computer program product at any possible technical detail level of integration. The computer program product may include a computer readable storage medium (or media) having computer readable program instructions thereon for causing a processor to carry out aspects of the present invention. The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks. The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While several embodiments have been described herein, it will be appreciated that elements from any given embodiment may be used with any one or more elements from any one or more of other embodiments described herein. Moreover, the descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. A computer system comprising:
a hardware processor and a memory coupled thereto, the memory comprising a database, the hardware processor configured to automatically:
randomly split the database into a plurality of sub-databases;
apply a database query to the plurality of sub-databases;

generate a plurality of respective estimated query response values for each sub-database based upon applying the database query;
calculate a median of the estimated query response values;
generate a probability distribution based upon the estimated query response values and the calculated median, wherein the processor is configured to generate the probability distribution so that the probability distribution at any point is given by $$\frac{P}{e^{-\epsilon l}}$$

wherein P is the probability distribution, ϵ is a predetermined parameter, and/is a number of points between a given estimated query response value and the median; and
select a final estimated query response value based upon the probability distribution.

2. The computer system of claim 1, wherein the hardware processor is configured to generate the probability distribution by at least weighting the plurality of estimated query response values based upon proximity to the calculated median; and wherein the processor is configured to select the final estimated query response by at least selecting one of the weighted plurality of respective estimated query response values based upon the weighting as the final estimated query response.

3. The computer system of claim 2, wherein the hardware processor is configured to generate the probability distribution by at least sampling each of the plurality of estimated query response values based upon $e^{-\epsilon|a_v - b_v|}$ wherein ϵ is a predetermined parameter, $a_v$ is a number of the estimated query response values greater than the selected estimated query response value, and $b_v$ is a number of the estimated query response values less than the selected estimated query response value.

4. The computer system of claim 3, wherein each of the plurality of estimated query response values is sampled from a set of possible query response values proportional to $e^{-\epsilon|a_v - b_v|}$.

5. The computer system of claim 3, wherein the hardware processor is configured to determine the pre-determined parameter ϵ according to $$\epsilon = \frac{\log_e |T| + 6}{m}$$

wherein T is a set of possible query response values and m is a random disjoint subset of n samples divided by t subsamples.

6. The computer system of claim 1, wherein the database comprises a medical database that includes medical data for patients.

7. The computer system of claim 1, wherein the database comprises a machine learning database.

8. A computer-implemented method for estimating a response to a database query, the method comprising automatically:
randomly splitting the database into a plurality of sub-databases;
applying a database query to the plurality of sub-databases;
generating a plurality of respective estimated query response values for each sub-database based upon applying the database query;
calculating a median of the estimated query response values;
generating a probability distribution based upon the estimated query response values and the calculated median, wherein the processor is configured to generate the probability distribution so that the probability distribution at any point is given by $$\frac{P}{e^{-\epsilon l}}$$

wherein P is the probability distribution, ϵ is a predetermined parameter, and l is a number of points between a given estimated query response value and the median; and
selecting a final estimated query response value based upon the probability distribution.

9. The computer-implemented method of claim 8, wherein generating the probability distribution comprises weighting the plurality of estimated query response values based upon proximity to the calculated median; and wherein selecting a final estimate query response comprises selecting one of the weighted plurality of respective estimated query response values based upon the weighting as the final estimated query response.

10. The computer-implemented method of claim 9, wherein the probability distribution is generated by at least sampling each of the plurality of estimated query response values based upon $e^{-\epsilon|a_v - b_v|}$ wherein ϵ is a predetermined parameter, $a_v$ is a number of the estimated query response values greater than the selected estimated query response value, and $b_v$ is a number of the estimated query response values less than the selected estimated query response value.

11. The computer-implemented method of claim 10, wherein each of the plurality of estimated query response values is sampled from a set of possible query response values proportional to $e^{-\epsilon|a_v - b_v|}$.

12. The computer-implemented method of claim 10, wherein the predetermined value of ϵ is determined according to $$\epsilon = \frac{\log_e |T| + 6}{m}$$

wherein T is a set of possible query response values and m is a random disjoint subset of n samples divided by t subsamples.

13. A computer-readable medium for estimating a response to a database query, the computer-readable medium comprising computer-executable instructions that when executed by a hardware processor cause the hardware processor to automatically perform operations comprising:
randomly splitting the database into a plurality of sub-databases;
applying a database query to the plurality of sub-databases;
generating a plurality of respective estimated query response values for each sub-database based upon applying the database query;
calculating a median of the estimated query response values;

generating a probability distribution based upon the estimated query response values and the calculated median, wherein the processor is configured to generate the probability distribution so that the probability distribution at any point is given by $$\frac{P}{e^{-\epsilon l}}$$

wherein P is we probability distribution, $\epsilon$ is a predetermined parameter, and l is a number of points between a given estimated query response value and the median; and
    selecting a final estimated query response value based upon the probability distribution.

14. The computer-readable medium of claim 13, wherein generating the probability distribution comprises weighting the plurality of estimated query response values based upon proximity to the calculated median; and wherein selecting a final estimate query response comprises selecting one of the weighted plurality of respective estimated query response values based upon the weighting as the final estimated query response.

15. The computer-readable medium of claim 14, wherein the probability distribution is generated by at least sampling each of the plurality of estimated query response values based upon $e^{-\epsilon|a_v - b_v|}$ wherein $\epsilon$ is a predetermined parameter, $a_v$ is a number of the estimated query response values greater than the selected estimated query response value, and $b_v$ is a number of the estimated query response values less than the selected estimated query response value.

16. The computer-readable medium of claim 15, wherein each of the plurality of estimated query response values is sampled from a set of possible query response values proportional to $e^{-\epsilon|a_v - b_v|}$.

17. The computer-readable medium of claim 15, wherein the predetermined value of $\epsilon$ is determined according to $$\epsilon = \frac{\log_e |T| + 6}{m}$$

wherein T is a set of possible query response values and m is a random disjoint subset of n samples divided by t subsamples.

* * * * *